United States Patent
Ali et al.

(10) Patent No.: US 11,098,140 B2
(45) Date of Patent: Aug. 24, 2021

(54) PRODUCTION OF 1-BUTENE AND ULTRA-HIGH-MOLECULAR-WEIGHT POLYETHYLENE

(71) Applicant: Saudi Arabian Oil Company, Dhahran (SA)

(72) Inventors: Ola S. Ali, Thuwal (SA); Wei Xu, Thuwal (SA); Hussain Al Yami, Thuwal (SA); Faisal Melebari, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/733,637

(22) Filed: Jan. 3, 2020

(65) Prior Publication Data
US 2021/0206890 A1    Jul. 8, 2021

(51) Int. Cl.
*C08F 110/02* (2006.01)
*C07C 2/06* (2006.01)
(Continued)

(52) U.S. Cl.
CPC .............. *C08F 10/02* (2013.01); *B01D 3/14* (2013.01); *B01J 19/0013* (2013.01); *B01J 19/1881* (2013.01); *B01J 19/26* (2013.01); *B01J 21/06* (2013.01); *B01J 31/22* (2013.01); *B01J 31/38* (2013.01); *C07C 2/34* (2013.01); *C08F 110/02* (2013.01); *B01J 2219/00092* (2013.01); *B01J 2219/00103* (2013.01); *B01J 2219/00182* (2013.01); *B01J 2219/00186* (2013.01); *B01J 2219/00247* (2013.01); *B01J 2219/00254* (2013.01); *B01J 2231/125* (2013.01); *B01J 2231/20* (2013.01); *B01J 2531/31* (2013.01);
(Continued)

(58) Field of Classification Search
CPC ... C07C 2/30; C07C 2/34; C07C 11/08; C08F 2/01; C08F 110/02
See application file for complete search history.

(56) References Cited

U.S. PATENT DOCUMENTS 493,339 A    3/1893 Phillips
1,028,012 A    5/1912 Foster
(Continued)

OTHER PUBLICATIONS

Forestiere, et al., "Oligomerization of Monoolefins by Homogenous Catalysts", Oil & Science and Technology Review de l'Institute: Francais du Petrole, vol. 64, No. 6. Nov. 2009, pp. 663-664, 20 pages.
(Continued)

*Primary Examiner* — Rip A Lee
(74) *Attorney, Agent, or Firm* — Fish & Richardson P.C.

(57) ABSTRACT

A system and method for producing 1-butene and ultra-high-molecular-weight polyethylene (UHMWPE), including feeding a catalyst, an antifouling co-catalyst, and ethylene to a reactor, and dimerizing ethylene into 1-butene and polymerizing a relatively small portion of the ethylene into UHMWPE. A product slurry including 1-butene and UHMWPE is discharged from reactor and UHMWPE is removed from the product slurry as a coproduct of the product 1-butene. The coproduct UHMWPE may be a byproduct that is a relatively small amount of the product slurry. The quantity of UHMWPE produced may be small in comparison to the quantity of 1-butene produced.

45 Claims, 5 Drawing Sheets

(51) Int. Cl.

| | | |
|---|---|---|
| *C07C 2/34* | (2006.01) | |
| *C08F 10/02* | (2006.01) | |
| *B01J 31/38* | (2006.01) | |
| *B01J 31/22* | (2006.01) | |
| *B01J 21/06* | (2006.01) | |
| *B01J 19/18* | (2006.01) | |
| *B01J 19/26* | (2006.01) | |
| *B01J 19/00* | (2006.01) | |
| *B01D 3/14* | (2006.01) | |
| *C07C 2/08* | (2006.01) | |
| *C07C 2/30* | (2006.01) | |

(52) U.S. Cl.
CPC .................. *C07C 2/06* (2013.01); *C07C 2/08* (2013.01); *C07C 2/30* (2013.01)

(56) References Cited

U.S. PATENT DOCUMENTS

| | | | | |
|---|---|---|---|---|
| 2,519,084 | A * | 8/1950 | Tull | F28D 7/08 165/158 |
| 2,930,784 | A * | 3/1960 | Hanson | C08F 4/22 528/503 |
| 3,441,631 | A | 4/1969 | Fernald et al. | |
| 3,502,741 | A | 3/1970 | Fernald et al. | |
| 5,292,837 | A | 3/1994 | Heinrich | |
| 6,306,981 | B1 * | 10/2001 | Brown | B01J 8/1827 422/132 |
| 6,767,975 | B1 | 7/2004 | Liu | |
| 7,157,532 | B2 * | 1/2007 | Payer | C08F 10/00 502/103 |
| 8,227,653 | B2 | 7/2012 | Weber et al. | |
| 8,821,800 | B2 * | 9/2014 | Benham | B01J 19/127 422/110 |
| 9,724,681 | B2 | 8/2017 | Lucciulli et al. | |
| 9,896,392 | B2 | 2/2018 | Meiswinkel et al. | |
| 9,919,298 | B2 * | 3/2018 | Schmidt | B01J 31/143 |
| 10,022,698 | B2 | 7/2018 | Shaikh et al. | |
| 10,105,693 | B2 * | 10/2018 | Schmidt | C08F 2/04 |
| 10,232,339 | B2 | 3/2019 | Bischof et al. | |
| 10,280,125 | B2 | 5/2019 | Sogo et al. | |
| 2004/0136882 | A1 * | 7/2004 | Verser | B01J 8/222 422/132 |
| 2016/0325274 | A1 | 11/2016 | Schmidt | |
| 2016/0367977 | A1 | 12/2016 | Shaikh | |
| 2017/0197892 | A1 | 7/2017 | Khawaji | |
| 2018/0327332 | A1 * | 11/2018 | Sogo | C07C 2/32 |
| 2019/0092707 | A1 * | 3/2019 | Melibari | C07C 2/30 |
| 2020/0001266 | A1 * | 1/2020 | Augier | B01J 19/245 |
| 2020/0354636 | A1 * | 11/2020 | Rajagopalan | C10G 3/57 |

OTHER PUBLICATIONS

Mahdaviani, et al, "Selective Ethylene Dimerization Toward 1-butene by a New Highly Efficient Catalyst System and Determination of Its Optimum Operating Conditions in a Buchi Reactor," International Journal of Chemical Engineering and Applications, vol. 1, No. 3, Oct. 2010, pp. 276-281, 6 pages.

* cited by examiner

US 11,098,140 B2

PRODUCTION OF 1-BUTENE AND ULTRA-HIGH-MOLECULAR-WEIGHT POLYETHYLENE

TECHNICAL FIELD

This disclosure relates to the oligomerization of ethylene.

BACKGROUND

Alpha-olefins (α-olefins) are a family of organic compounds that are alkenes with a chemical formula $C_xH_{2x}$ and having a double bond at the primary or alpha (a) position. This location of a double bond may enhance reactivity of the compound and thus make α-olefins useful for various applications. Certain linear short-chain α-olefins, such as 1-butene, 1-hexene, and 1-octene, may be utilized as a comonomer in the polymerization of ethylene into polyethylene to affect properties of the polyethylene.

A source of 1-butene is the mixed butenes fraction from the effluent of a hydrocarbon cracker, such as a steam cracker or fluidized catalytic cracker. However, isolating 1-butene from such an effluent requires complex processing that may be undesirable. Therefore, on-purpose production of 1-butene has been implemented.

Several commercial technologies selectively oligomerize ethylene into alpha-olefins such as 1-butene and 1-hexene. An example (a dimerization system) is the Alphabutol™ Process developed by the Institute Francais du Petrole (IFP) and described in A. Forestiere, et al., "Oligomerization of Monoolefins by Homogenous Catalysts", Oil & Science and Technology Review de l'Institute Francais du Petrole, pages 663-664 (Volume 64, Number 6, November 2009). The Alphabutol™ system employs a bubble-point reactor. In operation, the bubble-point reactor contains 1-butene as a process fluid to oligomerize ethylene selectively into 1-butene. The product 1-butene may be a process fluid in acting as a diluent or solvent.

In oligomerization systems that oligomerize (or dimerize) ethylene to produce α-olefins (e.g., 1-butene or 1-hexene), polymer formation fouls the oligomerization system. Polymer formation (e.g., polyethylene-based residues) may be due to long residence times in the oligomerization reactor and inadequate heat removal from the highly exothermic reactions. Chronic fouling caused by the polymer formation leads to more frequent system shutdowns and higher maintenance costs for removing adhered polymer residues. Polymer residues may build layer upon layer and eventually close off openings and ports in locations with fluid flow. Additionally, a polymer coating along the wall of a reactor (or in associated heat exchangers) may act as an insulator that can negatively affect heat transfer.

SUMMARY

An aspect relates to a method for producing 1-butene and ultra-high-molecular-weight polyethylene (UHMWPE), including feeding a catalyst (including a titanate compound), an antifouling co-catalyst, and ethylene to a reactor. The antifouling co-catalyst may be labeled as an antifouling agent (AFA) co-catalyst. The AFA co-catalyst has the structure:

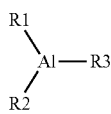

or its dimeric form, wherein Al is aluminum, and wherein R1, R2, and R3 are chemical groups. The method includes dimerizing ethylene into 1-butene in the reactor, polymerizing ethylene into polyethylene including UHMWPE in the reactor, discharging an effluent from the reactor having 1-butene and UHMWPE, and removing (e.g., filtering or centrifuging) UHMWPE from the effluent as coproduct UHMWPE.

Another aspect relates a method of producing 1-butene and UHMWPE, including reacting an antifouling compound (AFC) with a co-catalyst (aluminum alkyl) to give an AFA co-catalyst. The method includes providing the AFA co-catalyst, a catalyst, and ethylene to a reactor, and oligomerizing ethylene in the reactor via the catalyst and the AFA co-catalyst. The catalyst includes a titanate compound and is provided separate from the AFA co-catalyst. The oligomerizing involves dimerizing ethylene into 1-butene and polymerizing ethylene into UHMWPE. The method includes discharging a product slurry (including 1-butene and UHMWPE) from the reactor to a separator (e.g., solids separator to separate solids from liquid), which may be a separation device or separation vessel (e.g., filter, centrifuge, etc.) and removing UHMWPE as a coproduct from the product slurry via the separator.

Yet another aspect relates to a method for producing 1-butene and UHMWPE, including combining an AFC and a co-catalyst (aluminum alkyl) to give an AFA co-catalyst having the structure:

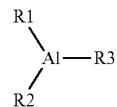

or its dimeric form, wherein Al is aluminum and R1, R2, and R3 are chemical groups. The method includes providing the AFA co-catalyst, a catalyst (titanate compound), and ethylene to a reactor, wherein the catalyst is provided separate from the AFA co-catalyst. The method includes oligomerizing ethylene in the reactor via the catalyst and the AFA co-catalyst, the oligomerizing including dimerizing ethylene into 1-butene and polymerizing ethylene into UHMWPE. The method includes discharging a product slurry from the reactor, the product slurry including 1-butene and UHMWPE. The method includes removing UHMWPE from the product slurry as coproduct.

Yet another aspect relates to a system for producing 1-butene and UHMWPE, including a reactor to oligomerize ethylene in presence of a catalyst and an AFA co-catalyst to 1-butene and UHMWPE. The catalyst includes a titanate compound. The AFA co-catalyst has the structure:

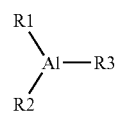

or its dimeric form, wherein Al is aluminum, and wherein R1, R2, and R3 are chemical groups. The system includes a separator (e.g., a solids separator to separate solids from liquid), such as a separation vessel (e.g., filter, centrifuge, etc.), to receive an effluent from the reactor and remove UHMWPE from the effluent as a coproduct and to discharge a product stream having 1-butene.

The details of one or more implementations are set forth in the accompanying drawings and the description below. Other features and advantages will be apparent from the description and drawings, and from the claims.

DETAILED DESCRIPTION

Figure 1:
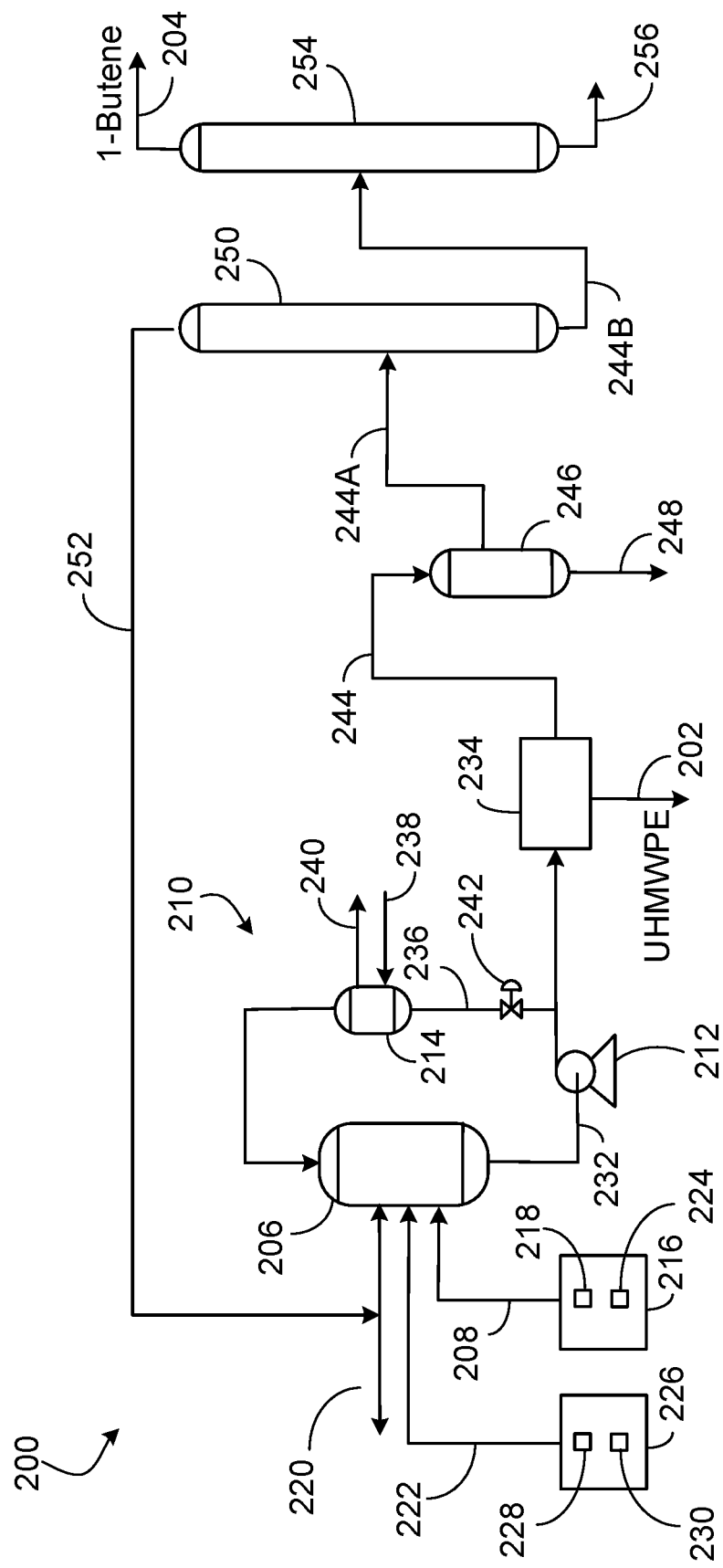
FIG. 1 is a diagram of an oligomerization system that produces coproduct UHMWPE along with the main product 1-butene.

Some aspects of the present disclosure are directed to ethylene oligomerization that produces 1-butene as a main product and ultra-high-molecular-weight polyethylene (UHMWPE) as a valuable byproduct (coproduct). The ethylene oligomerization (dimerization) may be for the on-purpose production of 1-butene. The ethylene oligomerization occurs in the presence of an ethylene oligomerization catalyst and Anti-Fouling-Agent (AFA™) co-catalyst. For exemplary descriptions of AFA™ and associated technology, see U.S. Pat. No. 10,280,125 B2 and US Published Application No. 2019/0092707 A1, both of which are incorporated herein by reference in their entirety.

While 1-butene can be a byproduct in effluent from a hydrocarbon cracker (e.g., steam cracking), 1-butene is primarily obtained by on-purpose production in the synthesis of 1-butene via ethylene dimerization. The cost of on-purpose production of 1-butene can be less than the cost of separating (e.g., via extractive distillation) 1-butene from hydrocarbon cracker effluent (mixed-C4 streams). The on-purpose production of 1-butene via ethylene dimerization may be beneficial in locations with access to competitively sourced ethylene and limited access to mixed-C4 streams. As for end-uses, 1-butene may be utilized, for example, as a comonomer in the production of linear low density polyethylene.

Alphabutol™ is a selective ethylene dimerization technology developed by IFP for the production of 1-butene. In Alphabutol™ and other oligomerization systems for the on-purpose production of 1-butene, a high selectivity for 1-butene is generally realized but polymerization occurs. The polymer (polyethylene) fouls equipment surfaces in the oligomerization system leading to system downtime to remove the polymer adhered to equipment internal surfaces. In response, the AFA™ technology is applied as a drop-in solution. The AFA™ technology reduces the amount of polymer produced and therefore lessens polymer fouling. The AFA™ technology also increases removability of the fouling polymer. System downtime is decreased. Consequently, annual production of 1-butene for the given oligomerization system utilizing AFA™ technology may be increased.

The present incorporation of AFA™ technology into the oligomerization system (e.g., Alphabutol™) may lower the molecular weight of the fouling polyethylene to that of UHMWPE. The molecular weight of the fouling polyethylene in the Alphabutol™ system without AFA™ is significantly greater than that of UHMWPE and thus not readily measurable. The present application of AFA™ to Alphabutol™ (or similar oligomerization systems) lowers the molecular weight of the formed polyethylene such that the molecular weight is detectable with conventional high-temperature gel permeation chromatography (HT-GPC). The polyethylene is thus identified as UHMWPE. In general, UHMWPE may have a molecular weight, for example, in a range of 2,000,000 atomic mass units (amu) to 7,500,000 amu, or in a broader range of 1,000,000 amu to 10,000,000 amu.

The Examples below confirmed that the present techniques provide for UHMWPE produced along with the product 1-butene. In Example 1, which utilized a batch laboratory reactor for dimerization of ethylene into 1-butene, the molecular weight of the polyethylene produced was in a range of 1,000,000 amu to 10,000,000 amu. The residence time in the semi-batch reactor was approximately 2 hours. The molecular weight varied with residence time in the reactor. In Example 2, which was implemented in an Alphabutol™ oligomerization reactor system (commercial unit), the molecular weight of the polyethylene produced was in a range of 1,000,000 amu to 10,000,000 amu.

With the AFA™ technology implemented in the on-purpose production of 1-butene by ethylene dimerization, such as in the Alphabutol™ system or similar oligomerization systems, benefits can include: (1) a prolonged reactor cooling-loop life cycle; (2) reduced frequency of reactor shutdown; and (3) increased 1-butene throughput. Therefore, higher 1-butene production rates may be realized. Also, unhindered (or less hindered) operation of any associated polyethylene operation utilizing the 1-butene as comonomer may be realized. An additional benefit associated with this AFA™ technology is co-production of the side product UHMWPE via the present techniques.

The polymer UHMWPE has characteristics of high-density polyethylene (HDPE) with added traits of resistance to concentrated acids, concentrated alkalis, and numerous organic solvents, as well as low moisture absorption and low coefficient of friction. UHMWPE is self-lubricating and resistant to abrasion. UHMWPE has generally been produced under restrictive conditions such as low temperature with low catalyst activity. The production cost of UHMWPE has been greater than production cost of HDPE, which limits UHMWPE applications. In present embodiments, UHMWPE is produced as a byproduct of 1-butene production. The amount of UHMWPE produced is less than the amount of 1-butene produced. The quantity of UHMWPE generated may be small in comparison to the quantity of 1-butene generated. Nevertheless, the coproduction and sale of this UHMWPE can improve the economics of the 1-butene production.

FIG. 1 is an oligomerization system 200 that produces coproduct UHMWPE 202 along with the main product 1-butene 204. The oligomerization reactor 206 performs catalyzed oligomerization of ethylene into 1-butene and higher α-olefins. The catalytic oligomerization involves the dimerization of ethylene into 1-butene and the polymerization of a smaller portion of the ethylene into UHMWPE. An antifouling agent (AFA) co-catalyst 208 fed to the reactor 206 promotes the catalyzed oligomerization but reduces the amount of polyethylene produced. In addition, the AFA co-catalyst 208 may provide for the polyethylene to more likely remain dispersed in the 1-butene and not adhere to equipment internal surfaces. Further, the AFA co-catalyst 208 provides for formation of the polyethylene as UHMWPE that is collected as the coproduct UHMWPE 202.

The coproduct UHMWPE 202 may be a byproduct that is a relatively small amount in comparison to the amount of 1-butene that is produced. The 1-butene may be the primary product. The amount of UHMWPE 202 may be less than 10% by weight (or less than 5% by weight) in comparison to the amount of 1-butene produced. In some examples, the amount of UHMWPE 202 produced is in a range of 3% to 8% by weight in comparison to the amount of 1-butene produced.

The UHMWPE 202 may have a molecular weight, for example, in a range of 2,000,000 amu to 7,500,000 amu, in a range of 1,000,000 amu to 10,000,000 amu. The UHMWPE 202 may be collected for distribution to a customer. For instance, the UHMWPE 202 can be transferred to a collection bin (vessel) before being bagged (placed into bags or other containers) for end users. Prior to bagging or distribution, the coproduct UHMWPE 202 may be treated with acid to remove metal residues (e.g., aluminum, titanium, etc.) from the UHMWPE 202. The oligomerization system 200 may include an extruder with pelletizing die to pelletize the UHMWPE 202 into pellets that are provided to end users.

The oligomerization reactor 206 may be a vessel having inlet nozzles for receipt of feed and an outlet nozzle for discharge of effluent. The nozzles may be flanged for coupling to conduits. The nozzles may have screwed threads or other coupling elements for connecting to conduits.

The reactor 206 may be a batch reactor or a continuous reactor such as a continuous stirred tank reactor (CSTR). A recirculating loop 210 (e.g., via a pump 212) may provide for the continuous stirring of the reactor 206 contents. The reactor 206 is typically an exothermic reactor with the reactions (e.g., oligomerization) in the reactor 206 being exothermic. The recirculating loop 210 may be a cooling loop in routing the recirculation through a heat exchanger 214 for temperature control of the reactor 206. In implementations, the reactor 206 is a vessel that is a bubble-point reactor in operation with 1-butene acting a diluent. A bubble-point reactor may be a reactor in which evaporative flashing occur simultaneously with the reaction to provide agitation of the reactor contents.

The AFA co-catalyst 208 may have the structure:

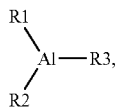

or its dimeric form, where Al is aluminum and R1, R2, and R3 are chemical groups. At least one of the chemical groups R1, R2, or R3 is an antifouling group. The chemical groups that are not an antifouling group, if any, are a hydrocarbyl group. The at least one of R1, R2, or R3 as an antifouling group may have the structure —O(($CH_2$)$_n$O)$_m$R4, where n is an integer in the range of 1 to 20, m is an integer in the range of 1 to 100, and R4 is a hydrocarbyl group. The at least one of R1, R2, or R3 as an antifouling group may have the structure —O((CRR')$_n$O)$_m$R", where R and R' each may be H or a hydrocarbyl group, R" is an alkyl, an amide, an amine, an alcohol, a silane, or other group, n is an integer in the range of 1 to 30, and m is an integer in the range of 1 to 50. Examples of hydrocarbyl groups for R and R' may be linear alkyl groups such as methyl, ethyl, propyl, or butyl groups, or branched alkyl groups such as isopropyl or isobutyl groups. The antifouling group (R1, R2, and/or R3) may be at least one of a phosphonium moiety, a sulfonate moiety, or a sulfonium moiety. The antifouling group (R1, R2, and/or R3) may be a chemical group with function or structure of a surfactant. The function of a surfactant may include to affect surface tension between the reaction media and the solid polyethylene polymer. A surfactant structure of the antifouling group (R1, R2, and/or R3) may be amphiphilic in containing both hydrophobic and hydrophilic portions. The surfactant function may include antifouling or providing for binding with the polymer (including polyethylene or UHMWPE) to hinder the growth of the polymer particles and so that the polymer particles do not settle (or less polymer particles settle).

The antifouling group (R1, R2, and/or R3) may be derived from an antifouling compound (AFC). The AFC may that is utilized to form the AFA co-catalyst 208 may have the phosphonium moiety, the sulfonate moiety, the sulfonium moiety, or a moiety having a surfactant function or structure, or a moiety that is the aforementioned structures —O(($CH_2$)$_n$O)$_m$R4 or —O((CRR')$_n$O)$_m$R".

The AFA co-catalyst 208 may be the reaction product of the AFC and the co-catalyst. The AFC can also be known as an antifouling agent (AFA). The AFC may be an additive that is mixed (reacted) with the co-catalyst aluminum alkyl. For the additive or precursor, the phrases "antifouling agent" (AFA) and "antifouling compound" (AFC) may be considered synonymous and can be in accordance with the AFA™ technology.

An AFA co-catalyst preparation section 216 combines (e.g., reacts) an AFC (or AFA) with a co-catalyst (e.g., aluminum alkyl) to give the AFA co-catalyst 208. Thus, the terminology utilized herein includes that an "AFC" is combined with a co-catalyst (e.g., aluminum alkyl) to give the "AFA co-catalyst" 208.

In some embodiments of the AFA co-catalyst preparation section 216, an inline mixer 218 (e.g., static mixer, impeller mixer, etc.) combines the AFC with the co-catalyst to give the AFA co-catalyst 208. The inline mixer 218 may generally provide adequate residence time for reaction of the AFC with the co-catalyst. In implementations, the reaction of the AFC with the co-catalyst (e.g., aluminum alkyl) may be relatively instant. The AFA co-catalyst 208 stream discharging from the inline mixer 218 may have excess or residual aluminum alkyl in addition to the AFA co-catalyst 208. The excess or residual aluminum alkyl in the AFA co-catalyst 208 stream did not react with the AFC and thus is not incorporated into the AFA co-catalyst 208 compound. This excess aluminum alkyl may be fed to the reactor 206 along with the AFA co-catalyst 208 (e.g., in the same stream).

The AFC that is combined (and reacted) with the co-catalyst aluminum alkyl may be or contain at least one of a phosphonium, a sulfonate, or a sulfonium. Examples of the AFC include a tetraalkyl phosphonium halide, a phosphonium malonate, a trihexyltetradecylphsophonium halide, a tetrabutylphosphonium halide, a tetrabutylphosphonium tetrahaloborate, a tetrabutylphosphonium halide, a tetrabutylphosphonium hexahalophosphate, a tetrabutylphosphonium tetrahaloborate, sodium dodecylbenzenesulfonate, sodium dioctylsulfonsuccinate, tetrabutylphosphonium methanesulfonate, tetrabutylphosphonium p-toluenesulfonate, hexadecyltrimethylammonium p-toluenesulfonate, 3-(dimethyl(octadecyl)ammonio)propane-1-sulfonate, 3,3'-(1,4-didodecylpiperazine-1,4-diium-1,4-diyl) bis(propane-1-sulfonate), or 3-(4-(tert-butyl)pyridinio)-1- propanesulfonate, or a compound with function(s) of surfactants, or any combinations thereof.

The AFC that is combined (and reacted) with the co-catalyst aluminum alkyl may have a moiety with the structure —HO$((CH_2)_nO)_m$R4, where n is an integer in the range of 1 to 20, m is an integer in the range of 1 to 100, and R4 is a hydrocarbyl group. The AFC may have a moiety with the structure —HO$((CRR')_nO)_m$R", where R and R' each may be H or a hydrocarbyl group, R" is an alkyl, an amide, an amine, an alcohol, a silane, or other group, n is an integer from 1 to 30, and m is an integer from 1 to 50. Examples of hydrocarbyl groups for R and R' may be linear alkyl groups such as methyl, ethyl, propyl, or butyl groups, or branched alkyl groups such as isopropyl or isobutyl groups.

The co-catalyst that is combined with the AFC may be an aluminum alkyl, such as trimethylaluminum (TMA), triethylaluminum (TEAL), tripropylaluminum, triisobutylaluminum (TIBAL), trihexylaluminum, trioctylaluminum, or methylaluminoxane (MAO). In particular embodiments, the co-catalyst is TEAL. The aluminum alkyl (e.g., TEAL) may be fed in neat form or fed diluted in a hydrocarbon solvent (e.g., hexane). In the case of TEAL, the TEAL may be diluted to a TEAL weight concentration less than 20% (or less than 10%) in the feed stream to the inline mixer 218.

In operation of the illustrated embodiment, ethylene 220, oligomerization catalyst 222 (e.g., a titanate compound), and the AFA co-catalyst 208 are fed via respective conduits to the oligomerization reactor 206. The motive force for flow of ethylene 220 to the reactor may be ethylene header pressure or an upstream compressor, and the like. A control valve disposed along the conduit conveying the ethylene 220 may control the amount of ethylene 220 fed to the reactor 206. The flow control of the ethylene 220 may take into account any recycle ethylene joining with the fresh ethylene 220.

One or more pumps 224 may provide motive force for flow of the AFA co-catalyst 208 to the reactor 206. In some implementations, a first pump 224 provides the AFC to the inline mixer 218 and a second pump 224 provides the co-catalyst (aluminum alkyl) to the inline mixer 218. In these implementations, the AFA co-catalyst 208 discharges from the inline mixer 218 to the reactor 206. The first pump 224 and the second pump 224 may each be, for example, a positive displacement pump or a centrifugal pump. In certain embodiments, the speed of each pump 224 may be controlled to give the desired flow rate of the AFC and co-catalyst, respectively, to the inline mixer 218, which gives the flow rate of the AFA co-catalyst 208 to the reactor 206. In other embodiments, respective control valves on each discharge conduit from the pumps 224 may modulate the flow rate of the AFC and co-catalyst to the inline mixer 218.

A catalyst feed section 226 may provide the catalyst 222 to the reactor 206. In certain implementations, the catalyst 222 may be dispersed or dissolved in a solvent (e.g., hexane) and fed in the catalyst 222 stream having the solvent to the reactor 206. The catalyst 222 may be a titanate compound, such as an alkyl orthotitanate having the structure Ti(OR)$_4$ in which R is independently at each occurrence a linear, branched, or cyclic alkyl group. In embodiments, each alkyl group R may have 2 to 8 carbon atoms, where each R group may be the same or different. Alkyl titanates as the catalyst 222 may include tetraethyl orthotitanate, tetraisopropyl orthotitanate, tetra-n-butyl orthotitanate (sometimes referred to as titanium butoxide), and tetra-2-ethylhexyl orthotitanate. In one implementation the titanate compound as the catalyst 222 is tetra-n-butyl orthotitanate.

A pump 228 may provide motive force for flow of the catalyst 222 to the reactor 206. In certain implementations, the catalyst feed section 226 includes a vessel 230 as a catalyst storage drum for supply of catalyst 222 via the pump 228 to the reactor 206. The pump 228 may be, for example, a positive displacement pump or a centrifugal pump. In certain embodiments, the speed of the pump 228 may be controlled to give the desired flow rate (amount) of the catalyst 222 provided to the reactor 206. In other embodiments, a control valve on the discharge conduit at the pump 228 may modulate the flow rate of the catalyst 222.

Operating variables of the oligomerization system 200 may be adjusted to affect the amount (yield) of UHMWPE 202 produced and the UHMWPE 202 properties (e.g., molecular weight). The yield and properties of the polymer UHMWPE 202 can be manipulated by changing reaction or process parameters, while also accounting for 1-butene productivity. Examples of such operating variables include feed molar ratios, reactor temperature, and so on.

The feed molar ratio of titanium (Ti) to aluminum (Al) to the reactor 206 is an operating variable that can affect the UHMWPE 202. The Ti/Al molar ratio may affect the amount and molecular weight of the UHMWPE 202 produced. The Ti/Al molar ratio may be in an exemplary range of 1:2 to 1:20. This feed molar ratio of Ti to Al to the reactor 206 may be adjusted to affect the amount of UHMWPE 202 produced or the molecular weight of the UHMWPE 202. In some implementations, the amount of UHMWPE 202 produced (the yield of UHMWPE 202) may vary inversely with the Ti/Al molar ratio.

The Ti/Al molar ratio may be altered by adjusting a ratio (e.g., mass ratio, volume ratio, molar ratio, etc.) of the AFA co-catalyst 208 to the catalyst 222 provided to the reactor 206. To adjust the molar ratio of Al to Ti fed to the reactor 206 to give a production amount or molecular weight of the UHMWPE 202, the techniques may include altering the flow rate (e.g., mass flow rate, volumetric flow rate, molar flow rate, etc.) of the AFA co-catalyst 208 provided to the reactor 206 or adjusting the flow rate of the catalyst 222 provided to the reactor, or both. Adjusting the feed molar ratio of Al to Ti may involve adjusting in the amount of co-catalyst combined (e.g., via the inline mixer 218) with the AFC in the AFA co-catalyst preparation section 216 to give the AFA co-catalyst 208.

Other molar ratios, such as the AFC/Ti molar ratio or AFA co-catalyst/Ti molar ratio, are also operating variables that may affect the UHMWPE 202. The AFC/Ti molar ratio may be the ratio of the molar rate of the AFC (that is combined with the co-catalyst at the inline mixer 218) to the molar rate of Ti in the catalyst 222 fed to the reactor 206. The AFA co-catalyst/Ti molar ratio may be the ratio of the molar rate of the AFA co-catalyst 208 to the molar rate of the catalyst 222.

The AFC/Ti molar ratio (or AFA co-catalyst/Ti molar ratio) can affect the molecular weight or other properties (e.g., entanglements or entanglement state) of the UHMWPE 202. The molecular weight of the UHMWPE 202 may vary inversely with the AFC/Ti molar ratio or the AFA co-catalyst/Ti molar ratio. The AFC/Ti molar ratio of feed to the reactor 206 may be adjusted or controlled by modulating the amount of AFC fed to the inline mixer 218, the amount of AFA co-catalyst 208 discharged from the inline mixer 218 to the reactor 206, or the amount of catalyst 222 fed to the reactor, and the like.

An exemplary range for the AFC/Ti molar ratio or the AFA co-catalyst/Ti molar ratio is 0.01 to 10. The "AFC" in the AFC/Ti molar ratio for this numerical range may refer to the moles of AFC fed to the inline mixer 218. Again, the feed molar ratio of AFC to Ti may be altered by adjusting the amount of AFC fed to the inline mixer 218 or by adjusting the amount of catalyst 126 fed to the reactor 206, or both. The feed molar ratio of AFA co-catalyst to Ti may be altered by adjusting the amount of AFA co-catalyst 208 fed to the reactor 206 or by adjusting the amount of catalyst 222 fed to the reactor 206, or both.

In the reactor 206, the ethylene 220 is oligomerized via the catalyst 222 and AFA co-catalyst 208 into 1-butene and higher α-olefins. Polymerization of ethylene 220 in the reactor 206 gives the coproduct UHMWPE. In general, more ethylene is oligomerized (dimerized) into 1-butene than is polymerized into the coproduct UHMWPE.

The operating pressure of the reactor 206 may be, for example, in the range of 5 bar to 100 bar. The operating temperature of the reactor 206 may be, for example, in a range of 30° C. to 180° C. Operating conditions outside of these ranges are contemplated, including in view of the specific design of the reactor system and concentrations of the reactants and catalysts.

In the illustrated embodiment, a product slurry 232 having the 1-butene (and higher α-olefins) and the UHMWPE discharges from a bottom portion of the reactor 206 as effluent into a discharge conduit to a separator 234. In some implementations, the amount of UHMWPE in the product slurry 234 may be less than 15 weight percent (wt %), less than 10 wt %, or less than 5 wt %. The separator 234 (e.g., a solids separator or solids/liquid separator) separates UHMWPE from the product slurry 232. The separator 234 may be a separation device, separation vessel, separator vessel, filter or filter vessel, centrifuge or centrifuge vessel, etc.

A portion of the product slurry 232 discharged from the reactor 206 may be routed via a recycle conduit as recycle 236 through the heat exchanger 214 for temperature control of the reactor 206. In the illustrated embodiment, the pump 212 provides motive force for the recycle 236 through the recirculation cooling loop 210.

A heat-transfer fluid supply 238 may be provided to the heat exchanger 214. A heat-transfer fluid return 240 may discharge from the heat exchanger 214. The heat transfer fluid may be, for example, cooling tower water or other coolant. The heat exchanger 214 may be, for example, a shell-and-tube heat exchanger or a plate-and-frame heat exchanger, and the like.

A control valve 242 may modulate the amount of recycle 236 for the reactor 206 temperature control. The flow rate of the recycle 236 may be modulated to control the reactor 206 operating temperature (e.g., of the reactor 206 contents) to a set point. The flow rate of heat transfer fluid through the heat exchanger 214 may be modulated for temperature control of the reactor 206. Multiple different control schemes for temperature control of the reactor may be applicable. The control valve 242 may be modulated and operate in tandem with the pump 212 to provide for consistent flow rate forward of the product slurry 232 to the separator 234.

The separator 234 removes UHMWPE from the product slurry 232. The removed UHMWPE is collected as coproduct UHMWPE 202. The UHMWPE 202 may be further processed. The coproduct UHMWPE 202 may be collected for distribution to a customer or end-user.

The separator 234 discharges a product stream 244 having the product 1-butene. The separator 234 may be a separator vessel having an inlet (e.g., inlet nozzle) to receive the product slurry 232. The separator vessel may have an outlet for discharge of the UHMWPE 202 and another outlet (e.g., outlet nozzle) for discharge of the product stream 244 (e.g., as filtrate).

For embodiments with the separator 234 as a filter, the filter may generally be a vessel with filter elements disposed in the vessel. The vessel may be a filter housing with filters or filter elements disposed therein. The filter vessel has an inlet (e.g., inlet nozzle) to receive the product slurry 232. In some examples, the inlet is on a side portion or end portion of the filter vessel. In operation, the filter elements may collect solid material including UHMWPE from the product slurry 232. The vessel has a solids discharge outlet for the UHMWPE 202 (e.g., from the filter elements). In some examples, the solids discharge outlet is on a bottom portion or end portion of the filter vessel. The solids discharge outlet can instead be on a side portion of the vessel. The filter vessel has a filtrate outlet for the product stream 244.

In certain implementations, the separator 234 as a filter may be a candle filter, a metal mesh filter, a plate filter, or a spinning (rotating) disk filter, and the like. A candle filter may be a pressure filter operating on a batch cycle and with the pressure elements having a cylindrical shape. For a metal mesh filter, the filter element(s) may be a metal mesh. In certain examples of a rotating disk filter, the filter elements may be multiple adjacent disks in series. In operation, the product slurry 232 may flow across the disks and solid material collected and dislodged between the disks. The filtrate product stream 244 may discharge from the end of the series of disks. Certain examples of the plate filter may be a plate-and-frame filter press. These various filter types are given as examples. Other filter types are applicable as the separator 234.

In some embodiments, the separator 234 may be a centrifuge, such as an industrial scale centrifuge. In implementations, the centrifuge can be electrically powered. In implementations, the centrifuge may generally be a continuous centrifuge although multiple batch or semi-batch centrifuges can be employed in parallel. A centrifuge may be a machine with a container that rotates in operation to apply centrifugal force to process contents of the container. In operation, a centrifuge may include a rapidly rotating vessel (container) that applies centrifugal force to the product slurry 232 to separate solids from liquid. In operation, the centrifuge may place the slurry in rotation around a fixed axis applying a force perpendicular to the axis of spin. The centrifuge can utilize sedimentation where the centrifugal acceleration causes denser substances and particles to move outward in the radial direction, and objects that are less dense are displaced and move to the center.

The separator 234 may be centrifuges of different rotor designs. The separator 234 may be, for example, a continuous tubular centrifuge. The separator 234 may be a filtration centrifuge or a sedimentation centrifuge. For the filtration centrifuge (also called screen centrifuge), a drum of the centrifuge is perforated and with a filter element (e.g., filter cloth, wire mesh, lot screen, etc.) inserted therein. In operation, the product slurry 232 may flows through the filter and the drum with the perforated wall from the inside to the outside. In this way, the solid material (UHMWPE) is restrained and can be discharged continuously or periodically. For a sedimentation centrifuge, the drum may be a solid wall (not perforated). The separator 234 may be a pendulum centrifuge, separator centrifuge (e.g., solid bowl or conical plate), tubular centrifuge, decanter centrifuge, and so on.

The product slurry 232 from the reactor 206 is processed in the separator 234 (e.g., filter or centrifuge) and discharges as the product stream 244. In particular, the product slurry 232 flows through the separator 234 that removes the UHMWPE 202 (collected as coproduct) and thus the incoming slurry 232 discharges as the product stream 244 having the product 1-butene. In the illustrated embodiment, the product stream 244 discharges from the separator 234 through a conduit to a thin-film evaporator 246 (or wiped-film evaporator) that removes heavy components 248. The removed heavy components 248 include, for example, heavy oligomers (e.g., C10 and plus). In some implementations, all or a majority of the heaving oligomers may each have ten carbons or more.

The product stream 244A discharged from the evaporator 246 flows through a conduit to a first distillation column 250 that removes unreacted ethylene. The removed ethylene is discharged overhead. The removed ethylene may be sent as recycle ethylene 252 to the oligomerization reactor 206. The recycled ethylene 252 may be added to a conduit conveying the ethylene 220 feed to the reactor 206.

In the illustrated implementation, the first distillation column 250 discharges the product stream 244B as a bottoms stream to a second distillation column 254. The second distillation column 254 removes heavy components 256 (e.g., including α-olefins having a greater molecular weight than 1-butene) discharged as a bottoms stream. The second distillation column 254 discharges overhead the product 1-butene 204.

The first distillation column 250 and the second distillation column 254 may each have distillation trays with each tray as a distillation stage that may involve heat transfer, mass transfer, and separation. The distillation columns 250, 254 may each have packing (instead of trays) that provides for theoretical distillation stages. The distillation columns 250, 254 may each have a reboiler heat exchanger and an overhead condenser heat exchanger. The distillation columns 250, 254 may each have a reflux system (e.g., including reflux drum vessel, reflux pump, etc.) that returns condensed overhead fluid to a side inlet nozzle on the distillation column.

The product 1-butene 204 discharged overhead from the second distillation column 254 may be condensed (e.g., in an overhead condenser) and distributed to users or customers. In some implementations, the 1-butene 204 may be provided to a polyethylene plant that polymerizes ethylene into polyethylene. In the polyethylene plant, the 1-butene 204 may be utilized as a comonomer in the polymerization of ethylene into polyethylene. In certain implementations, the polyethylene plant is adjacent or nearby the oligomerization system 200. In one implementation, the oligomerization system 200 may be characterized or labeled as partially integrated with the polyethylene production facility. In particular, the 1-butene 204 may be provided as a feedstock (comonomer) for the polymerization of ethylene into polyethylene in the polymerization reactor in the polyethylene plant.

Alphabutol® generally may utilize a homogeneous titanium-based promoted catalyst with aluminum alkyl (e.g., triethylaluminum or TEAL) as co-catalyst. The oligomerization reactor (dimerization reactor for 1-butene) may be a continuous reactor with external liquid (loop) circulation. In the external circulation, the reaction effluent may go through a recirculation loop equipped with a heat exchanger to remove the heat generated by the reaction and then the liquid effluent is recirculated back to the reactor. In some implementations of Alphabutol®, narrow ranges for operating conditions of the reactor include, for example, operating temperatures between 50° C. to 55° C. and operating pressures ranging from 2.2 millipascal (MPa) to 2.7 MPa. The conversion of ethylene to 1-butene can be set, for example, in the range of 80% to 85%. Depending on operating factors, the selectivity to 1-butene can reach up to 93% in commercial plant conditions. The reactor operating conditions and the conversion (selectivity) may be outside these ranges. The reaction is exothermic. The temperature control of the reactor may achieve the desired selectivity and reduce or eliminate side reaction.

As indicated, a hurdle facing Alphabutol® technology is the formation of polyethylene-based residues fouling the reactor, piping, and heat transfer surfaces. Despite the selective oligomerization catalyst, feed impurities (as well as catalytically active debris, such as rust) can act as free radical initiators for polymerization. Long residence times in the reactor and poor heat removal generally contribute to the polymer formation. The poor heat removal may be due to inadequate mixing of the reactor contents and also because of the accumulating polymer fouling acting as an insulator. The fouling causes frequent process shutdowns, higher maintenance costs, and financial losses due to operating below the nameplate capacity in both the 1-butene plant and the adjacent polyethylene plant if so disposed to utilize the 1-butene.

Aside from process and reactor optimizations to improve the mixing and heat removal, the use of an oligomerization or polymerization inhibitor as part of the catalyst system have been considered to overcome the chronic fouling issues in ethylene dimerization plants. This inhibitor option may be particularly attractive where the inhibitor option can be applied as a drop-in solution to existing 1-butene plants (e.g., Alphabutol® plants) without significant capital investment. Yet, such inhibitor additives and catalyst systems may operate at the expense of the dimerization reaction, reducing 1-butene selectivity. In contrast, the aforementioned AFA™ technology that provides an antifouling catalyst system as a fouling inhibitor option for ethylene oligomerization reactions does not deactivate the catalytic centers of the titanate catalyst or aluminum compounds (co-catalyst) and generally does not catalyze undesired reactions. The antifouling catalyst system of the AFA™ technology include an antifouling compound (AFC) to be paired with the co-catalyst and the oligomerization catalyst. For an Alphabutol® commercial 1-butene unit, the AFA™ technology may reduce polymer fouling by at least 60% and increase plant 1-butene capacity at least 80% due to lower shutdown frequencies.

The AFA™ technology (including the AFC and the AFA co-catalyst) with the present techniques provide benefits with respect to the polymer produced. First, with implementation of the AFC and resulting AFS co-catalyst, the polyethylene produced may more likely remain in the 1-butene and not adhere to equipment internal surfaces. Thus, the polyethylene may be more readily collected, for example, via a filter from a process stream without system shutdown.

Figure 2:
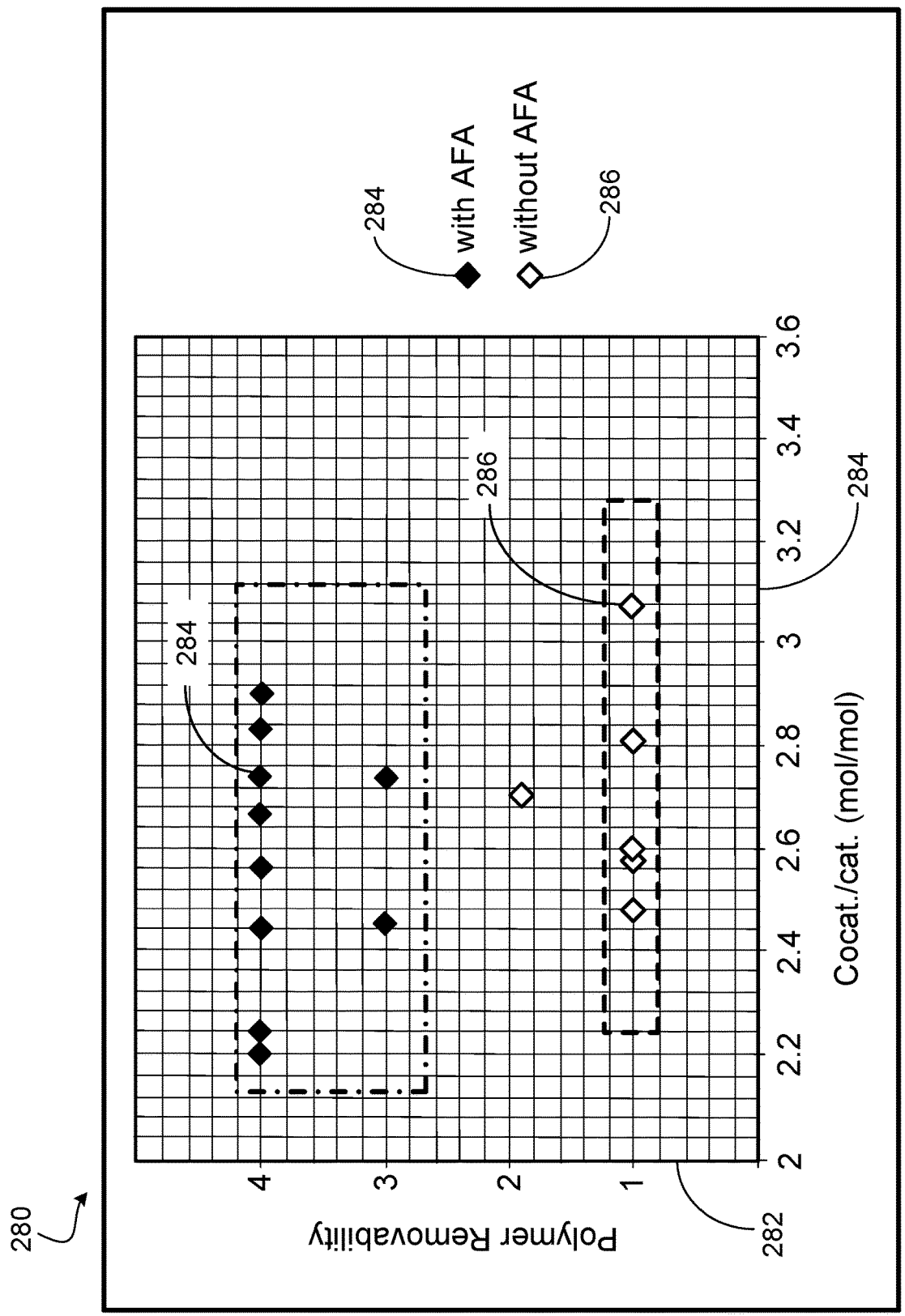
FIG. 2 is a plot of polymer (polyethylene) removability versus the molar ratio of co-catalyst to catalyst in an ethylene dimerization reactor.

Second, for the polyethylene (residue) that adheres to equipment surfaces, the AFS co-catalyst may provide for the polyethylene to be more easily removed from the equipment surfaces. FIG. 2 is a plot 280 of polymer (polyethylene) removability 282 versus the molar ratio 284 of co-catalyst to catalyst in an ethylene dimerization reactor. The polymer removability 282 is removability of the polymer adhered to internal surfaces of the reactor and associated piping. The numerical values for polymer removability 282 are: 4—removable by rubbing with a cloth softly; 3—removable by rubbing with a cloth strongly; 2—removable by brushing with steel wool; and 1—difficult to remove by brushing with steel wool. The plotted values indicated by reference numeral 284 are polymer removability 282 with the co-catalyst as AFA co-catalyst. The AFA co-catalyst is the reaction product of AFC and the co-catalyst aluminum alkyl. The plotted values indicated by reference numeral 286 are polymer removability 282 with the co-catalyst aluminum alkyl.

Third, with implementation of the AFA co-catalyst, the polyethylene produced can be UHMWPE. The utilization of the AFA co-catalyst for the ethylene dimerization reaction can reduce the molecular weight of the polymer (polyethylene) produced to the range of UHMWPE. By manipulating process parameters such as Ti/Al and Ti/AFC ratios, the yield and molecular weight of UHMWPE can be specified with the UHMWPE coproduced together with 1-butene.

The 1-butene unit generally suffers a chronic polymer fouling issues that reduces productivity and results in frequent shutdowns and higher maintenance costs. This translates to financial losses and also operating below the design capacity in the adjacent polyethylene plant that utilizes the 1-butene as comonomer. The complete elimination of polymeric fouling in oligomerization systems for 1-butene may not be feasible because of improper mixing, ineffective heat transfer, impurities in reaction media, and the like. Again, such fouling may reduce 1-butene yield and increase maintenance costs, both giving financial losses. However, by utilizing AFA™ technology, UHMWPE can be produced and sold to help mitigate the financial losses and increase the overall economic advantage of the process. The AFA™ technology can reduce polymeric fouling by at least 60%, as well as reduce the molecular weight of the fouling polymer for production and easier clean ups. While the polymer formation generally cannot be completely eliminated, the present techniques give process parameters to produce a polymer grade suited for sale as UHMWPE, which is a valuable by-product that boost the economics of the 1-butene process.

Figure 3:
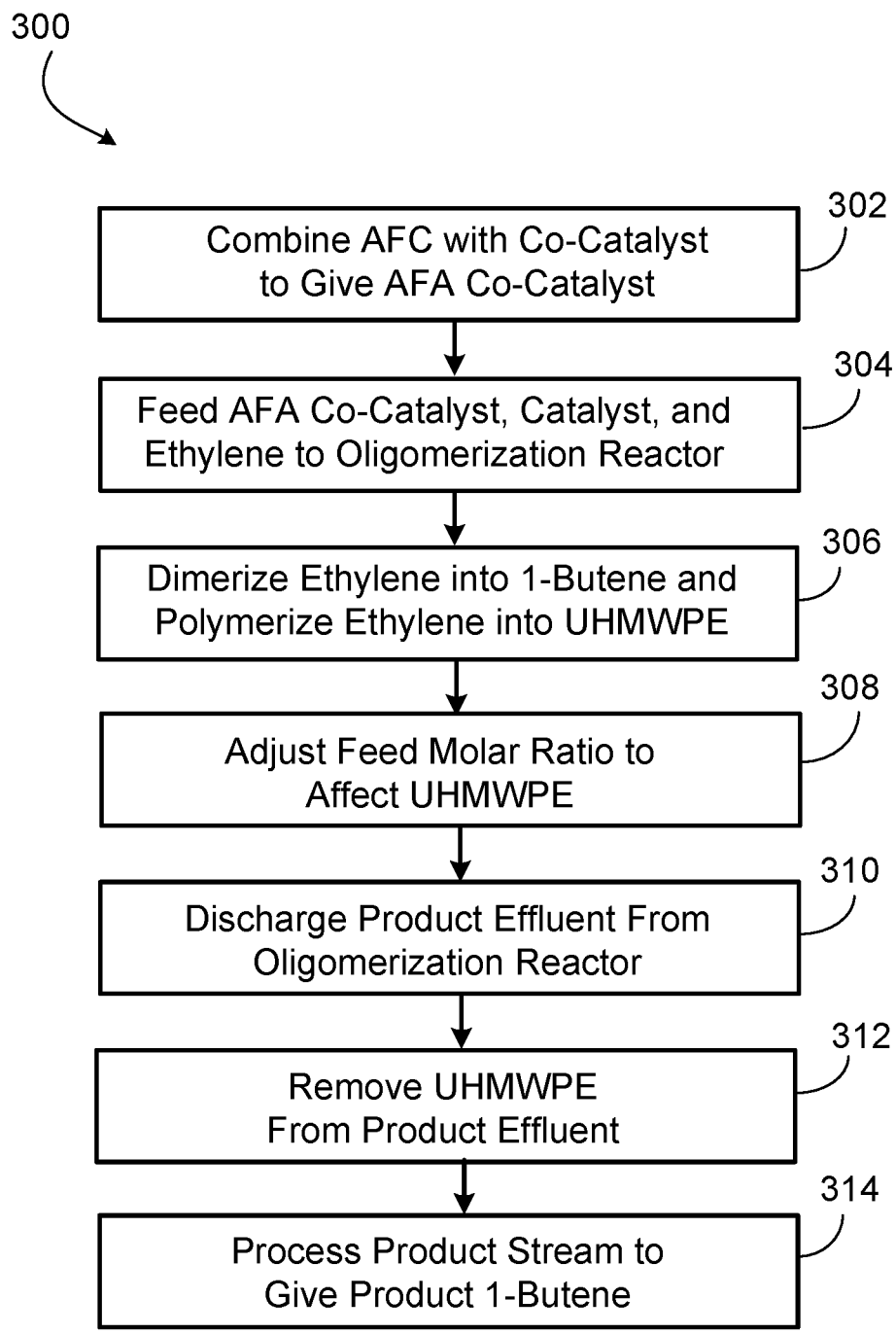
FIG. 3 is a block diagram of a method of producing 1-butene and UHMWPE.

FIG. 3 is a method 300 of producing 1-butene and UHMWPE. The method may be implemented in the on-purpose production of 1-butene, such as in an oligomerization system (e.g., Alphabutol® system) for the dimerization of ethylene into 1-butene. The AFA™ technology may be incorporated. The actions of method 300 in blocks 302 to 314, respectively, may be implemented in various orders or sequences, and may overlap or be contemporaneous. For instance, after startup of the oligomerization system as a continuous system, the discharge of product 1-butene (block 314) may be contemporaneous with combining AFC with co-catalyst (block 302).

At block 302, the method includes combining an AFC with a co-catalyst to give an AFA co-catalyst. As discussed, the AFC may be or contain, for example, a phosphonium, a sulfonate, or a sulfonium, or a compound with function(s) or structure of a surfactant. The function(s) of a surfactant may include to affect surface tension between the reaction media and the solid polyethylene polymer. Another surfactant function or structure may be the AFC being amphiphilic in containing both hydrophobic and hydrophilic groups making them good antifouling agents.

The co-catalyst may be TMA, TEAL, TIBAL, MAO, or other aluminum alkyl. The combining of the AFC with the co-catalyst may be performed in an inline mixer in certain embodiments. An AFC pump may provide for flow of the AFC to the inline mixer. A co-catalyst pump may provide for flow of the co-catalyst (aluminum alkyl) to the inline mixer. The combining of the AFC with the co-catalyst typically involves reacting the AFC with the co-catalyst to give the AFA co-catalyst that discharges from the inline mixer. The AFA co-catalyst stream that discharges from the inline mixer may have excess aluminum alkyl in addition to the AFA co-catalyst compound. The AFA co-catalyst can co-exist with conventional co-catalyst or as a fraction of total co-catalyst concentrations.

The AFA co-catalyst may have the structure:

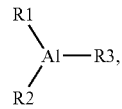

or its dimeric form, where at least one of R1, R2, or R3 is an antifouling group, such as a phosphonium moiety, a sulfonate moiety, a sulfonium moiety, or a moiety providing a surfactant function. The R1, R2, or R3 that are not an antifouling group, if any, is a hydrocarbyl group. In implementations, the R1, R2, or R3 as an antifouling group may have the structure —O((CH$_2$)$_n$O)$_m$R4, where n is an integer in a range of 1 to 20, m is an integer in a range of 1 to 100, and R4 is a hydrocarbyl group. In implementations, the at least one of R1, R2, or R3 as an antifouling group may have the structure —O((CRR')$_n$O)$_m$R", where R and R' each may be H or a hydrocarbyl group, R" is an alkyl, an amide, an amine, an alcohol, a silane, or other group, n is an integer in the range of 1 to 30, and m is an integer in the range of 1 to 50. Examples of hydrocarbyl groups for R and R' may be linear alkyl groups such as methyl, ethyl, propyl, or butyl groups, or branched alkyl groups such as isopropyl or isobutyl groups. Lastly, it should be noted that the AFC may have the phosphonium moiety, sulfonate moiety, sulfonium moiety, moiety providing a surfactant function, moiety having the aforementioned structure —O((CH$_2$)$_n$O)$_m$R4, or moeity having the aforementioned structure —O((CRR')$_n$O)$_m$R".

At block 304, the method includes feeding the AFA co-catalyst, catalyst, and ethylene to an oligomerization reactor. The AFA co-catalyst stream discharged from the inline mixer may be fed to the oligomerization reactor. The AFC pump and the co-catalyst pump upstream of the inline mixer may provide motive force for flow of the AFA co-catalyst discharged from the inline mixer to the oligomerization reactor. A catalyst pump may provide motive force for flow of catalyst to the oligomerization reactor. Motive force for flow of ethylene to the reactor may be the supplying ethylene header pressure or a compressor, and the like.

At block 306, the method includes dimerizing ethylene into 1-butene in the oligomerization reactor and polymerizing ethylene (e.g., a relatively small portion) into UHMWPE in the oligomerization reactor. Both the dimerization and the polymerization are generally exothermic. The reactor may be a batch reactor or a continuous reactor (e.g., CSTR). A recirculating cooling loop (e.g., via a pump, recirculation conduit, and heat exchanger) may provide for mixing and cooling of the reactor contents. An exemplary range for operating pressure of the oligomerization reactor is 5 bar to 100 bar. An exemplary range for operating temperature of the oligomerization reactor is 30° C. to 180° C. In implementations, the oligomerization reactor is a bubble-point reactor.

At block 308, the method includes adjusting a feed molar ratio(s) to affect the UHMWPE produced in the polymerization of ethylene in the oligomerization reactor. As discussed, feed molar ratios that may be adjusted to affect the amount or property (e.g., molecular weight) of the UHMWPE produced include Ti/Al, AFC/Ti, and AFA co-catalyst/Ti. The molecular weight of the UHMWPE may vary inversely with the AFC/Ti molar ratio or the AFA co-catalyst/Ti molar ratio. Initially, the feed molar ratios may be specified (e.g., in a recipe) for the startup of the dimerization (and polymerization) in the reactor in block 306. Subsequently, the feed molar ratios may be adjusted (block 308) contemporaneous with the actions in block 306 of dimerizing ethylene into 1-butene and polymerizing ethylene into polyethylene.

At block 310, the method includes discharging a product effluent from the oligomerization reactor. The product effluent may include 1-butene, higher α-olefins, UHMWPE, heavy components, unreacted ethylene, catalyst, etc. The product effluent may discharge from a bottom portion of the reactor, such a via a bottom outlet nozzle on the reactor vessel. In some implementations, a control valve and/or effluent centrifugal pump along the vessel discharge conduit at or near the bottom outlet nozzle (e.g., at the reactor vessel or on a pump discharge conduit of the effluent pump) may modulate the flow rate of the product effluent exiting from the reactor. As mentioned, a portion of the discharged product effluent may be recycled through a recirculation cooling loop back to the oligomerization reactor. The effluent pump may provide for flow of the portion of product effluent through the cooling loop and also for the primary flow of product effluent forward. The product effluent may flow to a separator, such as a filter or centrifuge.

At block 312, the method includes removing (e.g., filtering) UHMWPE from the product effluent and forwarding a product stream having the 1-butene. The method includes collecting the removed UHMWPE, which may be treated with acid to remove metal residues and/or pelletized. The UHMWPE may be placed in containers or bags and provided to a distributor, customer, or end user.

At block 314, the method includes processing the product stream to give 1-butene product. The processing the may initially include removing heavy components from the product stream, such as in a thin-film evaporator. In some embodiments, the processing my further include removing unreacted ethylene from the product stream in a first distillation column as an overhead discharge and removing additional heavy components in a second distillation column as a bottoms stream. In those embodiments, the product 1-butene may discharge overhead from the second distillation column.

The description below complements the above discussion. As indicated, embodiments of the present disclosure generally relate to processes and catalyst systems in ethylene oligomerization and, more specifically, relate to processes and antifouling catalyst systems in ethylene oligomerization which reduce polymerization. There may be a continual need for effective reactor systems and methods to prevent or reduce polymeric fouling on reactor system walls, piping, heat exchanger tubes, etc., while maintaining the desired oligomerization rate and selectivity to form 1-butene products.

According to embodiments, a system and method for selectively producing 1-butene is provided. The process includes combining at least one antifouling agent or antifouling compound and at least one aluminum alkyl compound to form an antifouling feed stream. Bringing the at least one antifouling agent or antifouling compound into contact with the at least one co-catalyst (aluminum alkyl compound) forms at least one antifouling compound (antifouling agent co-catalyst) including a central aluminum atom bound to an R1 group, bound to an R2 group, and bound to an R3 group, or derivatives thereof. An atom in the chemical groups R1, R2, or R3 optionally binds to the aluminum atom to form a chelate ring. The process further includes feeding the antifouling feed stream (antifouling agent co-catalyst), a catalyst having at least one titanate compound, and ethylene into a reactor to dimerize ethylene. The catalyst having the at least one titanate compound is fed as a stream separate from the antifouling feed stream. In certain embodiments, the molar ratio of the at least one antifouling agent (antifouling compound) and the at least one aluminum alkyl compound may be varied in real-time via an inline mixer to adjust a ratio of the formed antifouling agent co-catalyst and residual aluminum alkyl compound in the antifouling feed stream.

The terms "antifouling agent" or "antifouling compound" (AFC) may refer to compounds added to the AFA co-catalyst preparation section (e.g., 216 of FIG. 1 or 50 of FIG. 5) to provide for prevent or reduce polyethylene fouling in the oligomerization reactor system and to improve polyethylene removability from the oligomerization reactor system. The term "AFA co-catalyst" and the unabbreviated "antifouling agent co-catalyst" may refer to aluminum compounds which are formed in the AFA co-catalyst preparation section by the reaction of the AFC and co-catalyst (aluminum alkyl).

Embodiments are directed to reactor and catalyst systems which may be utilized in promoting ethylene oligomerization, such as the dimerization of ethylene to form 1-butene, while reducing reactor fouling caused by polymerization. These catalyst systems are sometimes referred to in this disclosure as "antifouling ethylene oligomerization catalyst systems" or "antifouling catalyst systems." The antifouling catalyst systems described may include at least one titanium based catalyst, at least one co-catalyst, and at least one antifouling agent (antifouling compound) or derivative thereof. Embodiments of the antifouling catalyst systems described may include at least one titanate compound, at least one aluminum alkyl compound as the co-catalyst, and at least one antifouling agent (antifouling compound or AFC) or derivative thereof. The antifouling catalyst systems may further include one or more ether compounds. The antifouling catalyst systems may be used to selectively oligomerize ethylene to produce 1-butene and other higher α-olefins, while reducing undesirable polymerization, sometimes referred to in this disclosure as "fouling." For example, reactor fouling may occur due to the formation of solid polyethylene-based residues which may reduce fluid flow and partially or fully block fluids in a reactor system from flowing at a desired rate. It should be understood that the "antifouling ethylene oligomerization catalyst systems" or "antifouling catalyst systems" described may not completely eliminate fouling during a reaction. However, these catalyst systems reduce fouling and make any formed polymer easier to remove as compared with catalyst systems which do not include an antifouling agent (antifouling compound) as described in the present disclosure. Also, while the catalyst systems of the present disclosure may be useful in ethylene oligomerization reactions, such as ethylene dimerization to form 1-butene, these catalyst systems may also be useful for the catalysis of other chemical reactions, and the antifouling catalyst systems described in this disclosure should not be considered limited in their use to the dimerization of ethylene to 1-butene.

The 1-butene may be produced through ethylene dimerization. The ethylene may be brought into contact with the antifouling catalyst system to dimerize ethylene to form 1-butene. In certain embodiments, the ethylene and an antifouling catalyst system are supplied to a reactor and mixed. The reaction may be performed as a batch reaction or as a continuous process reaction, such as a continuous stir tank reactor. According to embodiments, the pressure in the reactor may be from 5 bar to 100 bar, and the reactor temperature may be from 30° C. to 180° C. However, process conditions outside of these ranges are contemplated, especially in view of the specific design of the reactor system and concentrations of the reactants and catalysts.

In operation, a feed system (e.g., FIG. 5) provides a catalyst and an AFA co-catalyst to the reactor during ethylene oligomerization. The AFA co-catalyst is formed from a co-catalyst and an antifouling agent (antifouling compound or AFC). The catalyst includes generally one or more titanate compounds. The combination of the AFA co-catalyst and the catalyst forms the antifouling catalyst system.

Figure 4:
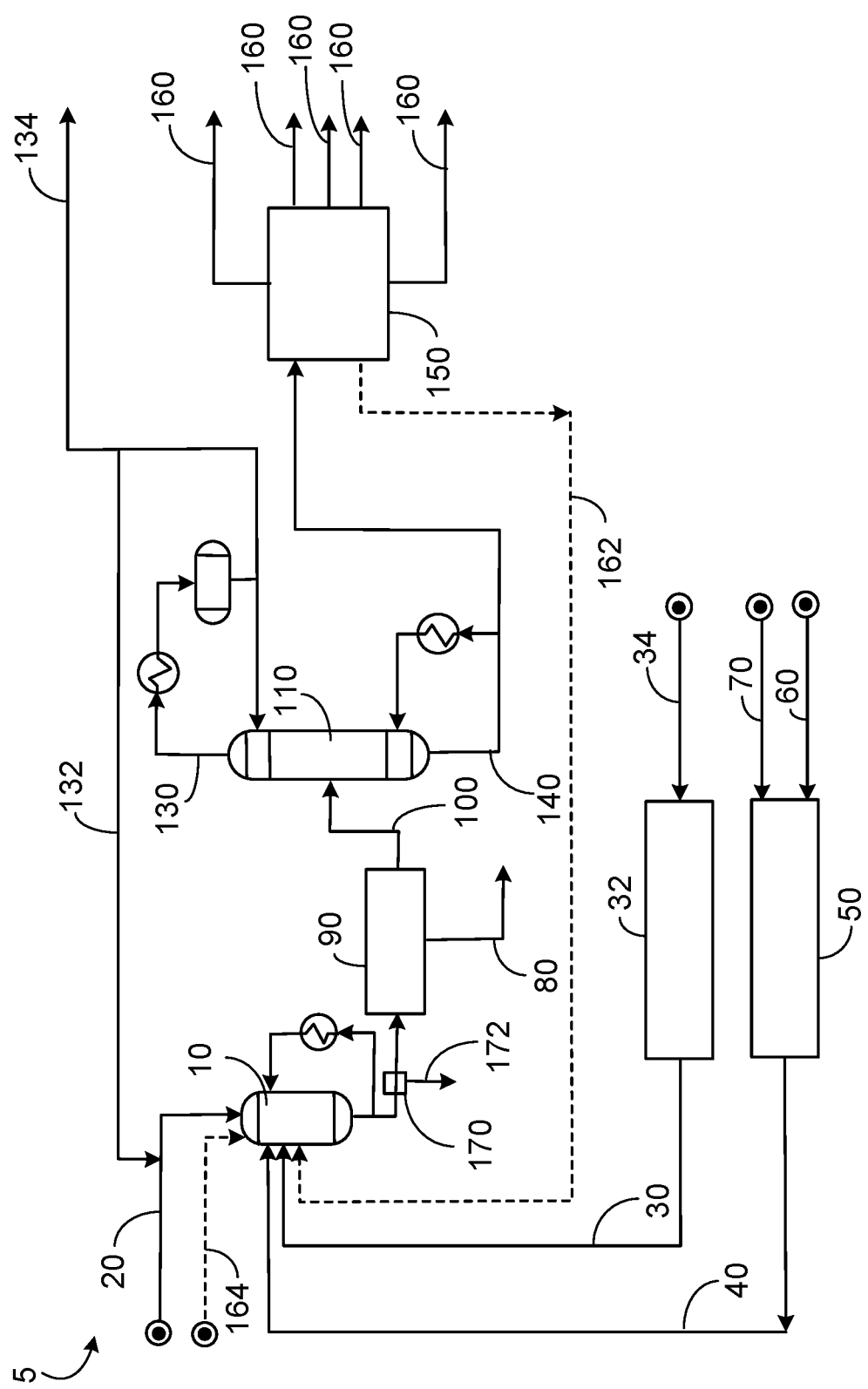
FIG. 4 is a diagram of an ethylene oligomerization system.

FIG. 4 is an ethylene oligomerization system 5, which may be the same or similar as the oligomerization system 200 of FIG. 1. The reactor 10 may be analogous to the oligomerization reactor 206 of FIG. 1. Ethylene is fed into a reactor 10 as an ethylene feed 20 where the catalyzed oligomerization of the ethylene to 1-butene and other higher α-olefins occurs. Additionally, the reactor 10 has separate inputs for a catalyst stream 30 including the catalyst and an antifouling feed stream 40 including the AFA co-catalyst. The antifouling feed stream 40 includes the mixture of the at least one antifouling agent (antifouling compound or AFC) and at least one co-catalyst, the co-catalyst including at least one aluminum alkyl compound. The mixture is prepared in the AFA co-catalyst preparation section 50 by combining the antifouling compound (AFC) provided in an AFC make-up stream 60 and the at least one co-catalyst provided in a co-catalyst make-up stream 70 at an appropriate ratio. The separate inputs provides for interaction between the catalyst and the AFA co-catalyst to occur within the reactor 10. Additionally, the catalyst stream 30 is provided to the reactor 10 from a catalyst preparation section 32 fed from a catalyst make-up stream 34.

Subsequent to the reactor 10, the spent catalyst 80 is separated from the stream exiting the reactor 10 in a catalyst removal section 90. The remaining reactor exit stream after the spent catalyst removal serves as a process stream 100 being provided to an ethylene recycle column 110. The ethylene recycle column 110 may be analogous to the first distillation column 250 of FIG. 1. The ethylene recycle column 110 separates residual ethylene 130 from the process stream 100 for recycle as an ethylene recycle stream 132 back to the reactor 10 for oligomerization or to be purged from the system as an ethylene purge stream 134 and utilized as fuel. The non-ethylene stream exiting the ethylene recycle column 110 is further provided as a product process stream 140 to a distillation section 150 for further separation of components. For example, the distillation section 150 may separate the product process stream 140 into a plurality of product streams 160 including 1-butene, 1-hexene, 1-octene, 1-decene and a heavy cut. This separation may be achieved in accordance with standard techniques known now or in the future to one having skill in the art. It will be appreciated that separation of the product process stream 140 into various components may be adjusted based on the make-up of the product process stream 140 and the particular chemical species or species within the product process stream 140 desired for further use or collection. The distillation section 150 may also separate solvents from the product process stream 140, which may be recycled back to the reactor 10 as a solvent recycle stream 162. Solvents may also be introduced to the reactor 10 directly with a solvent makeup stream 164.

The polymerization of ethylene into UHMWPE occurs in the reactor 10. A separator 170 (e.g., filter, centrifuge, etc.) removes UHMWPE 172 from the stream exiting the reactor 10. The separator 170 may be analogous to the separator 234 of FIG. 1. The UHMWPE 172 may be treated with acid to remove metal residues and may be pelletized. The UHMWPE 172 may be collected for distribution or sale to customers or end-users.

Figure 5:
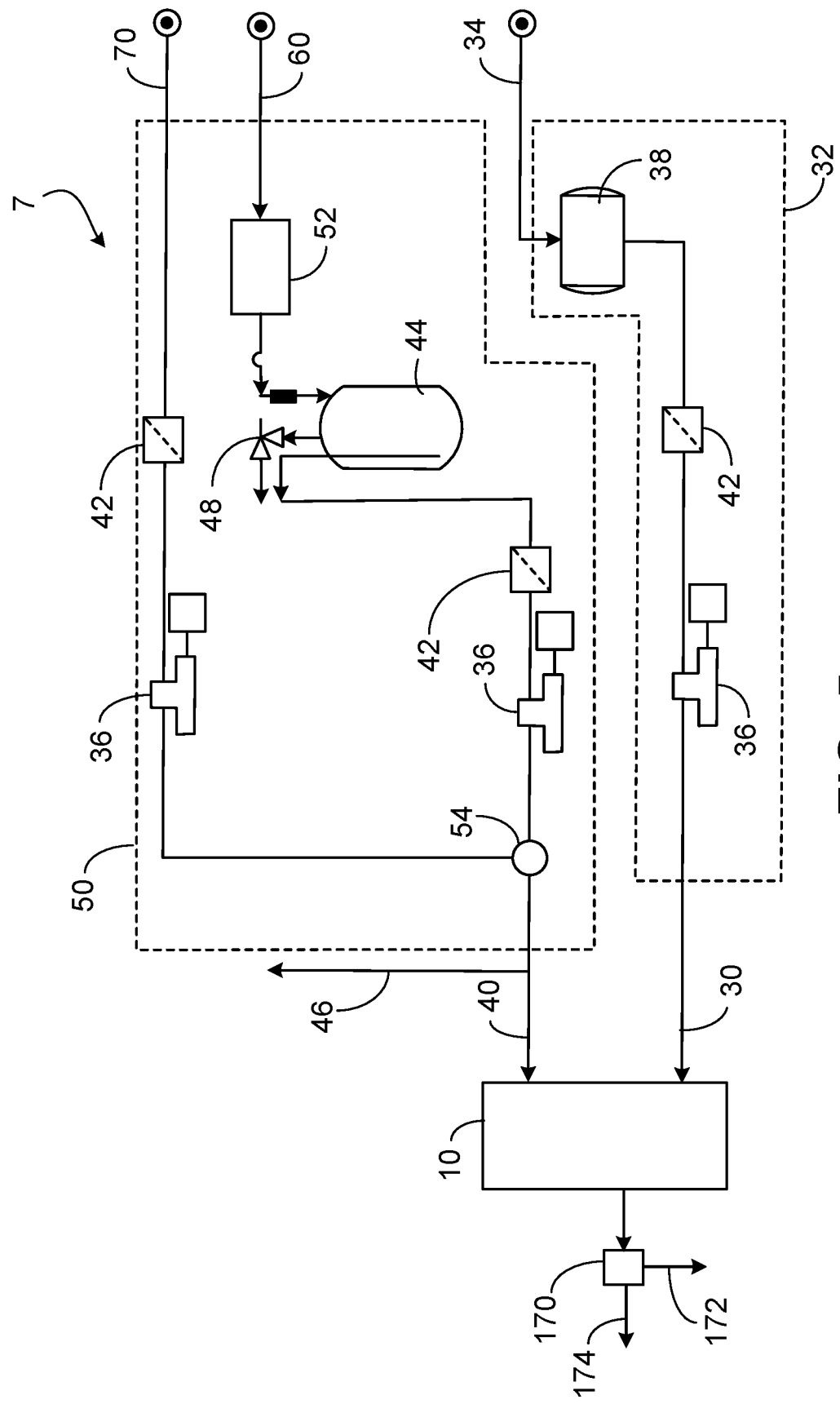
FIG. 5 is a diagram of a feed system for the oligomerization reactor of FIG. 4.

FIG. 5 is a feed system 7 for the reactor 10. The feed system 7 is depicted to give exemplary detail (embodiments) of reactor feed sub-systems upstream of the reactor 10. The feed system 7 includes the catalyst preparation section 32 (e.g., catalyst feed section, catalyst injection system, etc.) that provides a catalyst stream 30 to the reactor 10. The catalyst preparation section 32 shown in FIG. 5 may be a more detailed depiction of an example of the catalyst feed section 226 of FIG. 1. The feed system 7 includes an AFA co-catalyst preparation section 50 that may also be labeled as an AFA co-catalyst injection system that prepares and injects the AFA co-catalyst to the reactor 10. The AFA co-catalyst preparation section 50 shown in FIG. 5 may be a more detailed depiction of an example of the AFA co-catalyst preparation section 216 of FIG. 1.

The feed system 7 facilitates production of UHMWPE in the oligomerization reactor 10. Downstream of the reactor 10 and feed system 7, a separator 170 (e.g., filter) removes UHMWPE 172 from the reactor 10 effluent and discharges a stream 174 having 1-butene. The stream 174 discharged from the separator 170 may be processed to isolate the product 1-butene to be provided to end-users. The removed UHMWPE 172 may be treated and collected for distribution to customers or end-users.

The feed system 7 provides the catalyst feed stream 30 into the reactor 10. The catalyst is provided from a catalyst source to the reactor 10 by a pump 36 or other locomotion means. In at least one embodiment, a catalyst storage drum 38 provides a reservoir of catalyst for supply to the reactor 10 on an on-demand basis. The catalyst storage drum 38 maintains a reservoir of catalyst for supply to the reactor 10 and is resupplied from the catalyst make-up feed 34. Further, in embodiments, a filter 42 is provided in-line in the conduit coupling the catalyst source or catalyst storage drum 38 to the reactor 10. The filter 42 provides removal of particulates or other foreign components from the catalyst stream.

Throughout this disclosure, the discussed catalyst includes at least one titanate compound. However, other catalysts maybe utilized in the ethylene oligomerization reaction and the catalyst preparation section 32. For example, catalyst systems based on transition metal complexes such as nickel, chromium, zirconium, or other metal complexes may be used in addition to or as a substitute for the discussed titanate compound.

The antifouling feed stream 40 into the reactor 10 is provided. The at least one AFA co-catalyst is formulated from a combination of the at least one co-catalyst and the at least one AFC via an inline mixer 54 provided with feeds of the co-catalyst 70 and the AFC 60. In one or more embodiments, the co-catalyst 70 and the AFC 60 are each provided to the inline mixer 54 by a respective dedicated pump 36 (or other locomotion means) that provides locomotive force to convey the combined product of the inline mixer (antifouling feed stream 40) into the reactor 10. The separate dedicated pumps 36 or other locomotion means for each of the co-catalyst and AFC facilitates each to be provided at a quantitative measure (weight, volume, concentration) that may be changed or varied independently based on the process conditions over time.

In various embodiments, the inline mixer 54 may be an impeller mixer or a static mixer with internal mixing elements. The inline mixer 54 may include one or more internal mixing elements with a helical, ribbon-like, or plater type geometry. The internal mixing elements provide a method for delivering two streams of fluid into the static mixer which are continuously blended by the non-moving mixing elements during passage of the two streams through the static mixer. As such, a stream of the co-catalyst and a stream of the AFC may be provided to the inline mixer 54 and be ejected as the antifouling feed stream 40 having the AFA co-catalyst without the need for storing a pre-batch mixture including the AFA co-catalyst. The inline mixer 54 also provides the ability to combine three or more streams including one or more AFCs in combination with the co-catalyst depending on the desired AFA co-catalyst for formation.

In one or more embodiments, the at least one AFC is brought into contact with the at least one co-catalyst at specified ratio for the current process conditions in the inline mixer 54 to form the antifouling feed stream 40 including a mixture of the at least one AFA co-catalyst and residual co-catalyst or antifouling compound if provided in excess. The reaction of the AFC and co-catalyst to form the AFA co-catalyst varies based on the specific structure of the AFC. For example, when the AFC is an alcohol, the reaction includes protonolysis of the alkyl group of the co-catalyst. The reaction of forming the AFA co-catalyst from the AFC and the co-catalyst may result in the formation of gas, which may be vented downstream of the inline mixer 54 as an off-gas stream 46 or from the reactor 10. The specific gas generated for discharge as the off gas stream 46 varies depending on the structure of the co-catalyst. For example, triethylaluminum generates ethane gas during the AFA co-catalyst formation. The antifouling feed stream 40 resulting from the mixture of the AFC and co-catalyst is provided to the reactor 10 as a separate injection from the catalyst. In contrast, the providing of the AFA co-catalyst and the catalyst as a combined stream may cause an increase in fouling.

In various embodiments, the at least one AFC and co-catalyst are mixed in the inline mixer 54 at molar ratios of AFC to co-catalyst ranging, from example, from 0.01 to 0.18, or alternatively ranging from 100% AFC to 100% co-catalyst. The flow through the inline mixer 54 may be only AFC when so desired. The flow through the inline mixer may be only co-catalyst when so desired.

Combining the at least one AFC and the at least one co-catalyst inline at the time of introduction to the reactor provides flexibility in the amount of AFC and co-catalyst reacted to from the AFA co-catalyst. The desired quantitative measure of AFA co-catalyst may be formed by limiting the amount of AFC or co-catalyst introduced to the inline mixer 54. Excess AFC or co-catalyst introduced to the inline mixer 54 beyond that which reacts with the other species is introduced into the reactor 10 along with the formed AFA co-catalyst. For example, if excess co-catalyst is introduced to the inline mixer 54, the product fed to the reactor 10 would include the formed AFA co-catalyst along with the residual co-catalyst. The feed of the AFC to the inline mixer 54 can be cut off or adjusted and only the co-catalyst or desired level of formed AFA co-catalyst injected into the reactor 10.

In operation for some embodiments, the level of AFA co-catalyst introduced into the reactor may be reduced or minimized during certain intervals. For example, AFA co-catalyst is useful to activate ethylene oligomerization catalyst (catalyst), but also may undesirably passivate the reactor during fresh reaction start up. The concentration level of AFA co-catalyst may be reduced or minimized during reaction start up to avoid passivation of the reactor by introducing a reduced percentage of AFC compared to normal operation thereby generating less co-catalyst while maintaining flow of the co-catalyst. Once the desired AFA co-catalyst concentration has been reached during the reaction startup, the feed of AFC can be terminated to the inline mixer 54 to preclude the introduction of further AFA co-catalyst until warranted. Similarly, the concentration level of AFA co-catalyst may also be reduced during heat exchanger integration to avoid passivation of the heat exchangers.

In operation for certain embodiments, the level of co-catalyst introduced into the reactor may be increased during certain process conditions. For example, in a reactor condition where the reaction is lost due to contaminations, heat exchanger integrations, or combinations thereof, the concentration of the co-catalyst in the reactor may typically be increased. The mixing via inline mixer 54 of separate streams of co-catalyst and AFC allows for an increase in the co-catalyst provided to the reactor while maintaining or reducing the total formation of AFA co-catalyst subsequently provided to the reactor. Maintaining or reducing the AFC fed to the inline mixer 54 has a commensurate effect on the total production of AFA co-catalyst regardless of any increase in the provision of co-catalyst to the inline mixer 54. This adjustable AFA co-catalyst production afforded by the inline mixer 54 prevents an AFA co-catalyst build up in the reactor to undesired levels as a result of the necessary increased co-catalyst provision to restart the ethylene dimerization reaction. In certain instances, the AFA co-catalyst may have a maximum efficacy in a range of 1 to 10 parts per million (ppm) in the reactor.

Elevated AFA co-catalyst levels may also lead to additional complications with the reaction in system 5. Specifically, an elevated AFA co-catalyst concentration may increase the difficulty in removing fouling polymers deposited on the reactors and heat exchangers as well as change the nature of the formed polymer. Conversely, desired or specified AFA co-catalyst levels may promote removal of fouling polymer and give the formed polymer as UHMWPE.

As commercially available AFCs may contain water, the AFC 60 is passed through a drying bed 52 to remove or reduce the water content in the AFC. The dried AFC 60 is subsequently provided to an AFC feed tank 44 to store the dried AFC 60 until demanded for mixing with the co-catalyst 70 in the inline mixer 54. A filter 42 is provided in-line in the conduit conveying the dried AFC 60. A filter 42 may also be provided in-line in the conduit conveying the co-catalyst 70. In one or more embodiments, the water content in the AFC provided to the AFC feed tank 44 is maintained lower than approximately 0.3 wt % because an excessive amount of water could deactivate the antifouling catalyst system. In further embodiments, the water content in the AFC is maintained lower than approximately 0.1 wt %. The drying beds 52 contain a drying agent to remove water from the AFC make-up stream 60. In various embodiments, the drying agent is molecular sieves or sodium (Na) supported on alumina or silica. It will be appreciated by one skilled in the art that other means of drying the AFC are known and those means are equally envisioned.

In some implementations, the AFC feed tank 44 has a pressure relief valve 48. The pressure relief valve 48 is operational to allow the antifouling compound feed tank 44 to vent in the event of excessive pressurization. To avoid rupture of the AFC feed tank 44, the pressure relief valve 48 may allow quickened venting of the AFC feed tank 44 in the event of excessive off-gas formation or insufficient off-gas collection or typical venting.

As described previously in this disclosure, embodiments of the described antifouling catalyst systems may include one or more titanate compounds. The titanate compounds serve as the catalyst. While several titanate compounds may be included in the antifouling catalyst system, in some embodiments a single titanate compound may be included in the antifouling catalyst system. In one or more embodiments, the titanate compound may be an alkyl orthotitanate. An alkyl orthotitanate has the structure $Ti(OR)_4$ in which R is independently at each occurrence a linear, branched, or cyclic alkyl group. In one or more embodiments, each alkyl group may have from 2 to 8 carbon atoms, where each R group may be the same or different. Suitable alkyl titanates may include tetraethyl orthotitanate, tetraisopropyl orthotitanate, tetra-n-butyl orthotitanate (sometimes referred to as titanium butoxide), and tetra-2-ethylhexyl orthotitanate in one or more embodiments, the titanate compound of the antifouling catalyst system consists of tetra-n-butyl orthotitanate.

As also described previously in this disclosure, embodiments of the described antifouling catalyst systems may include one or more aluminum alkyl compounds. The aluminum alkyl compounds serve as the co-catalyst and are combined with the antifouling compound to form the AFA co-catalyst. The aluminum alkyl compounds may have a structure of $AlR'_3$ or $AlR'_2H$, where R' is a linear, branched, or cyclic alkyl group comprising from 1 to 20 carbon atoms, or an aluminoxane structure, that is, a partial hydrolysate of trialkylaluminum compounds. It will be appreciated that each R' may be unique. For example, and not by way of limitation, suitable aluminum alkyl compounds may include trialkylaluminums. The trialkylaluminums may be TMA, TEAL, tripropylaluminum, TIBAL, trihexylaluminum, trioctylaluminum, or MAO. In one or more embodiments, the aluminum alkyl compound of the antifouling catalyst system consists of TEAL.

In embodiments, the antifouling compound to be combined with the aluminum alkyl compound to form the AFA co-catalyst may be selected from one or more of a phosphonium (including [R1R2R3R4]+), sulfonium ([ROSO$_2$]$^-$), sulfonate ([R1R2R3S]$^+$), and a fouling-preventing surfactant including nonionic surfactants, anionic surfactants, cationic surfactants, and zwitterionic surfactants. Examples of nonionic surfactants include polyoxyethylene monoalkyl ethers, polyoxyethylene dialkyl ethers, polyoxypropylene monoalkyl ethers, polyoxypropylene dialkyl, polyoxyethylene-polyoxypropylene-polyoxyethylene block copolymers, polyoxypropylene-polyoxyethylene-polyoxypropylene block copolymers, oligoglucoside monoalkyl ethers, polyoxyethylene mono(alkylphenyl) ethers, glycerol alkyl esters, N,N,N',N'-tetra(polyoxyalkylene)-1,2-ethylenediamines, and polyoxyethylene sorbitan alkyl esters such as polysorbate. Examples of anionic surfactants include sodium stearate and sodium 4-(5-dodecyl) benzenesulfonate. Examples of cationic surfactants include dimethyldioctadecylammonium chloride and dimethyldioctadecylammonium bromide.

Examples of zwitterionic surfactants include 3-[(3-cholamidopropyl)dimethylammonio]-1-propanesulfonate, cocamidopropyl hydroxysultaine, cocamidopropyl betaine, and phosphatidylethanolamine.

The antifouling catalyst systems may comprise one or more AFA co-catalysts or derivatives thereof. As used herein, a derivative refers to a derivative structure of an AFA co-catalyst, such as a dimer, trimer, oligomer, polymer, isomer, hydrolysate of an AFA co-catalyst described in this disclosure. It will be appreciated that differing antifouling compounds will form differing AFA co-catalysts when combined with the aluminum alkyl compounds. In one or more embodiments, an AFA co-catalyst may have a central aluminum molecule bonded to all three of a first chemical group R1, a second chemical group R2, and a third chemical group R3. A generalized chemical structure of an AFA co-catalyst with R1, R2, and R3 representing chemical groups that may be antifouling groups (derived from the antifouling compound) is:

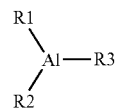

In implementations, one or more of R1, R2, and R3 are antifouling groups comprising the structure —O(($CH_2$)$_n$O)$_m$R4, where n is an integer of from 1 to 20. In various embodiments, n is an integer of from 1 to 10, 1 to 5, or 2 to 3, m is an integer of from 1 to 100, and R4 is a hydrocarbyl group. In various embodiments, n is an integer of from 1 to 10, 1 to 5, or 2 to 3 and m is an integer of from 1 to 50, 1 to 20, or 1 to 10. The central aluminum atom is bonded to a terminal oxygen of the antifouling group opposite to the R4 hydrocarbyl group. As used throughout this disclosure, a hydrocarbyl group refers to a chemical group that consists of hydrogen and carbon atoms. For example, a hydrocarbyl group may be linear, branched, or cyclic, and may comprise one or more alkyl moieties, one or more alkenyl moieties, one or more alkynyl moieties, aryl moieties, or combinations thereof. In various embodiments, R4 may be a hydrocarbyl group having from 1 to 100 carbon atoms, from 2 to 50 carbon atoms, or from 8 to 28 carbon atoms.

As previously described in this disclosure, one, two, or all three of R1, R2, and R3 may be the antifouling groups having the structure —O(($CH_2$)$_n$O)$_m$R4. In embodiments described in this disclosure, the chemical groups R1, R2, or R3 that do are not the antifouling group, if any, are hydrocarbyl groups. For example, R1 may be an antifouling group with the structure —O(($CH_2$)$_n$O)$_m$R4 and R2 and R3 may be hydrocarbyl groups. In another embodiment, R1 and R2 may be antifouling groups with the structure —O(($CH_2$)$_n$O)$_m$R4, and R3 may be a hydrocarbyl group. In another embodiment, R1, R2, and R3 may be antifouling groups with the structure —O(($CH_2$)$_n$O)$_m$R4. When at least two of R1, R2, and R3 are hydrocarbyl groups, they may be identical to one another or may be different hydrocarbyl groups. Also, when two or more of R1, R2, or R3 are antifouling groups, the antifouling groups may be identical or chemically different. However, each antifouling group will have the generic structure —O(($CH_2$)$_n$O)$_m$R4. In various embodiments, R1, R2 and R3 that are hydrocarbyl groups may each have from 1 to 100 carbon atoms, from 2 to 75 carbon atoms, or from 2 to 50 carbon atoms. For example, the hydrocarbyl groups may be linear alkyl groups such as methyl, ethyl, propyl, or butyl groups, or branched alkyl groups such as isopropyl or isobutyl groups.

In embodiments, the AFA co-catalyst may be present as a dimerized form, referred to herein as an example of a derivative of an AFA co-catalyst. A prepared AFA co-catalyst may be present in both dimerized and non-dimerized, that is, non-bonded, form. In a dimerized embodiment, bonds may form between the central aluminum atoms of an AFA co-catalyst molecule and an oxygen atom of a neighboring AFA co-catalyst molecule. It should be understood that while the central aluminum atoms are bonded to the oxygen atom in the neighboring AFA co-catalyst that is the nearest to its central aluminum atom, in other embodiments, this may not be the case, and the central aluminum atom may bond with an oxygen atom of a neighboring AFA co-catalyst which is not the nearest to its central aluminum atom.

In one or more embodiments, the AFA co-catalyst may be present in different isomer states. An isomer is an example of a derivative structure of an AFA co-catalyst. For example, the central aluminum atom of an AFA co-catalyst may be bonded to two oxygen atoms of a single antifouling group to form a chelate ring.

In implementations, the AFC of the antifouling catalyst system may include a phosphonium antifouling compound. The phosphonium antifouling compound may be combined with the aluminum alkyl compound to form the AFA co-catalyst. As used in this disclosure, phosphonium antifouling compounds include the phosphonium structure ($[PR1R2R3R4]^+$, where R1, R2, R3, and R3 represent H, alkyl, aryl, halide and/or chemical groups which may contain other moieties, and the various R groups may be identical or different from one another. Generally, phosphonium antifouling compounds may be introduced into the antifouling catalyst system as phosphonium salts, where the phosphonium cation forms an ionic bond with an anion compound. As used in this disclosure, phosphonium antifouling compounds include phosphonium salts or zwitterionic compounds comprising phosphonium moieties.

Phosphonium antifouling compounds include, for example, tetraalkyl phosphonium salts. For example, the antifouling compound may include tetraalkyl phosphonium halides (such as tetrabutyl phosphonium halide), phosphonium malonates (such as tetrabutylphosphonium malonate), trihexyltetradecylphsophonium halides (such as trihexyltetradecylphsophonium bromide), tetrabutylphosphonium halides (such as tetrabutylphosphonium iodide), tetrabutylphosphonium tetrahaloborates (such as tetrabutylphosphonium tetrafluoroborate), tetrabutylphosphonium halides (such as tetrabutylphosphonium chloride), tetrahutylphosphonium hexahalophosphates (such as tetrabutylphosphonium hexafluorophosphate), or tetrabutylphosphonium tetrahaloborates (such as tetrabutylphosphonium tetrafluoroborate). As used throughout this disclosure, a halide may include fluoride, chloride, bromide, or iodide (and "halo" may include the elements fluorine, chlorine, bromine, or iodine). In one or more embodiments, the groups, that is, R1, R2, R3, and R4, may be linear, branched, or cyclic alkyls, alkenyls, alkynyls, or aryls, and the R groups may be identical or different from one another.

In certain embodiments, the AFC of the antifouling catalyst system includes one or more sulfonate antifouling compounds. The sulfonate AFC may be combined with the aluminum alkyl compound to form the AFA co-catalyst. Generally, sulfonate AFCs may be introduced into the antifouling catalyst system as a sulfonate salt, where the sulfonate anion forms an ionic bond with a cation compound. As used in this disclosure, sulfonate AFCs include sulfonate salts or zwitterionic compounds having sulfonate moieties.

Sulfonate AFCs may include sulfonate salts. For example, sulfonate AFCs may include, without limitation, sodium dodecylbenzenesulfonate, sodium dioctylsulfonsuccinate, tetrabutylphosphonium methanesulfonate, tetrabutylphosphonium p-toluenesulfonate, and (hexadecyl)trimethylammonium, p-toluenesulfonate. In other embodiments, suitable antifouling compounds may include non-salt sulfonates, that is, zwitterionic sulfonates which do not dissociate into a separated cation and anion. For example, non-salt sulfonates suitable as antifouling compounds include, without limitation, 3-(dimethyl(octadecyl)ammonio)propane-1-sulfonate, 3,3'-(1,4-didodecylpiperazine-1,4-diium-1,4-diyl)bis(propane-1-sulfonate)-, and 3-(4-(tert-butyl)pyridinio)-1-propanesulfonate.

The AFC of the antifouling catalyst system may be one or more sulfonium antifouling compounds. The sulfonium AFC may be combined with the aluminum alkyl compound to form the AFA co-catalyst. Generally, sulfonium AFcs may be introduced into the antifouling catalyst system as sulfonium salts, where the sulfonium cation forms an ionic bond with an anion compound. As used in this disclosure, sulfonium AFCs include sulfonium salts or zwitterionic compounds having sulfonium moieties.

In implementations, the antifouling catalyst systems may include more than one molecular species of AFA co-catalyst. For example, some AFA co-catalysts may have one, two, or three antifouling groups, while others have a different number of antifouling groups. The mixture of these AFA co-catalyst species may form a bulk AFA co-catalyst which can be characterized by its bulk molar ratio of hydrocarbyl groups to antifouling groups which are attached to the central aluminum atoms, respectively. For example, if half of the AFA co-catalyst has one antifouling group and two hydrocarbyl groups, and, the other half of the AFA co-catalyst has two antifouling groups and one hydrocarbyl group, then the bulk molar ratio of hydrocarbyl groups to antifouling groups would be 1:1 because there is a bulk equal amount of hydrocarbyl groups to antifouling groups. In various embodiments, the bulk molar ratio of hydrocarbyl groups to antifouling groups may be from be from 1:3 to 2:1, 1:2 to 2:1, or from 1:1 to 2:1.

In some implementations, the antifouling catalyst system may include one or more ether compounds to reduce the formation of polymers. The one or more ether compounds may include cyclic ethers such as, but not limited to, tetrahydrofliran (THF), 1,4-dioxane, tetrahydropyran (THP), or combinations thereof.

As discussed, the antifouling catalyst systems may include titanate compounds, aluminum alkyl compounds, and AFA co-catalysts. In embodiments, the molar ratio of total titanate compounds to total aluminum alkyl compounds may be from 1:10 to 1:1.5, from 1:3 to 1:1.5, or from 1:3 to 1:2.

In various embodiments, the molar ratio of the AFCs brought into contact with the aluminum alkyl compound to the sum of the aluminum alkyl compounds brought into contact with the aluminum alkyl compound and additionally provided into the reactor may be from 0.001:1 to 0.5:1, from 0.01 to 0.18, or from 0.01 to 0.13. In various embodiments, the molar ratio of total titanate compounds to total ether compounds may be from 1:20 to 1:0, from 1:10 to 1:1, or from 1:8 to 1:3.

The molar ratios of components of the antifouling catalyst systems described previously are representative of the total amount of each component of the antifouling catalyst system relative to the total amount of titanate compound or aluminum alkyl compound, where the "total" amount refers to the molar amount of all species of the antifouling catalyst system which may be considered as a particular component type, that is, titanate compound, aluminum alkyl compound, ether compound, or AFC. The total amount of a component may include two or more chemical species which are titanate compounds, aluminum alkyl compounds, ether compounds, or antifouling compounds, respectively.

Without being bound by theory, it is believed that heteroatoms such as oxygen or nitrogen of the AFA co-catalysts may form weak coordination with the titanate compound utilized as the catalyst in the catalyst system. It is believed that, in one or more embodiments, the alkyl groups or other relatively long-chained groups of the AFA co-catalysts may serve in some capacity to prevent ethylene access to the catalytic center of the titanate compound. The restriction of access of the ethylene to the titanate catalytic site may reduce the polymerization of ethylene and thus reduce reactor fouling.

In implementations, the introduction of the AFA co-catalyst into the catalyst system may suppress polymer formation while not greatly reducing catalytic activity of 1-butene formation. In one embodiment, polymer formation (fouling) may be reduced by at least 5%, 10%, 20%, 30%, 40%, 50%, 60%, 70%, 80%, 90%, or even 95% by the inclusion of an AFA co-catalyst. In one embodiment, 1-butene production may be increased, stay the same, or may decrease by less than or equal to 50%, 40%, 30%, 20%, 10% or even 5% by the inclusion of an AFA co-catalyst. In some embodiments, AFA co-catalysts may both reduce the polymer formation, such as by at least 5%, 10%, 20%, 30%, 40%, 50%, 60%, 70%, 80%, 90% or even 95%, and increase, not effect, or decrease 1-butene production rate by less than or equal to 50%, 40%, 30%, 20%, 10% or even 5%. Reduction in polymer formation rates and catalytic activity on a percentage basis are based on catalyst systems which include one or more AFA co-catalysts described as compared with catalyst systems which are void of an AFA co-catalyst.

An embodiment is a method for producing 1-butene and UHMWPE, including feeding a catalyst, an AFA co-catalyst, and ethylene to a reactor, wherein the catalyst includes a titanate compound, and wherein the AFA co-catalyst has the structure:

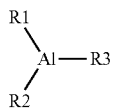

or its dimeric form, wherein Al is aluminum, and wherein R1, R2, and R3 are chemical groups. In implementations, at least one of R1, R2, or R3 are an antifouling group having the structure —O((CH2)nO)mR4, wherein n is an integer in a range of 1 to 20, m is an integer in a range of 1 to 100, and R4 is a hydrocarbyl group, wherein the chemical groups R1, R2, or R3 that are not an antifouling group, if any, are a hydrocarbyl group. The method may include combining an AFC and a co-catalyst to give the AFA co-catalyst, wherein the co-catalyst comprises an aluminum alkyl, and wherein feeding the catalyst comprises feeding the catalyst to the reactor separate from the AFA co-catalyst. In implementations, the AFC may be at least one of a phosphonium, a sulfonate, or a sulfonium. In implementations, the AFC may be a tetraalkyl phosphonium halide, a phosphonium malonate, a trihexyltetradecylphsophonium halide, a tetrabutylphosphonium halide, a tetrabutylphosphonium tetrahaloborate, a tetrabutylphosphonium halide, a tetrabutylphosphonium hexahalophosphate, a tetrabutylphosphonium tetrahaloborate, sodium dodecylbenzenesulfonate, sodium dioctylsulfonsuccinate, tetrabutylphosphonium methanesulfonate, tetrabutylphosphonium p-toluenesulfonate, hexadecyltrimethylammonium p-toluenesulfonate, 3-(dimethyl(octadecyl)ammonio)propane-1-sulfonate, 3,3'-(1,4-didodecylpiperazine-1,4-diium-1,4-diyl)bis(propane-1-sulfonate), or 3-(4-(tert-butyl)pyridinio)-1-propanesulfonate, or compounds with functions of surfactants, or any combinations thereof. The functions of surfactants may include a surfactant function that is antifouling or provide for binding with the polymer to hinder the growth of the polymer particles and so that the polymer particles do not settle (or less polymer particles settle).

The method includes dimerizing ethylene into 1-butene in the reactor, polymerizing ethylene into polyethylene including UHMWPE in the reactor, discharging an effluent from the reactor having 1-butene and UHMWPE, and removing (e.g., filtering) UHMWPE from the effluent as coproduct UHMWPE. The method may include adjusting a feed molar ratio of Ti to aluminum (Al) to the reactor to affect molecular weight of the polyethylene to give the UHMWPE or to affect an amount of UHMWPE produced, or a combination thereof. The method may include adjusting a molar ratio of the AFA co-catalyst to Ti fed to the reactor to affect molecular weight of the polyethylene to give the UHMWPE, wherein the molecular weight of the polyethylene varies inversely with the molar ratio of the AFA co-catalyst to Ti. The method may include adjusting a ratio of a molar rate of the AFC combined with the co-catalyst to a molar rate of Ti in the catalyst fed to the reactor to affect molecular weight of the UHMWPE, wherein the molecular weight of the UHMWPE varies inversely with the ratio. The method may include collecting the coproduct UHMWPE for distribution to a customer or end-user. The method may include treating the coproduct UHMWPE with acid to remove metal residues including aluminum and titanium from the coproduct UHMWPE. The method may include pelletizing the coproduct UHMWPE.

Another embodiment is a method of producing 1-butene and UHMWPE, including reacting an AFC with a co-catalyst (aluminum alkyl) to give an AFA co-catalyst, providing the AFA co-catalyst, a catalyst, and ethylene to a reactor, and oligomerizing ethylene in the reactor via the catalyst and the AFA co-catalyst. The catalyst includes a titanate compound and is provided separate from the AFA co-catalyst. The oligomerizing involves dimerizing ethylene into 1-butene and polymerizing ethylene into UHMWPE. The method includes discharging a product slurry (including 1-butene and UHMWPE) from the reactor to a separator (e.g., filter) and removing UHMWPE from the product slurry via the separator as a coproduct. In implementations, the AFC may be or contain at least one of a phosphonium, a sulfonate, or a sulfonium. As discussed, the AFA co-catalyst may have the structure:

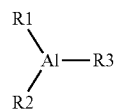

or its dimeric form, wherein Al is aluminum and R1, R2, and R3 are chemical groups. In some implementations, at least one of the chemical groups R1, R2, or R3 are an antifouling group that is at least one of a phosphonium moiety, a sulfonate moiety, or a sulfonium moiety, and wherein the chemical groups R1, R2, or R3 that are not an antifouling group, if any, are a hydrocarbyl group. The method may include altering a flow rate of the AFA co-catalyst provided to the reactor or a flow rate of the catalyst provided to the reactor, or both, to adjust a molar ratio of the AFA co-catalyst to titanium (Ti) fed to the reactor to give a molecular weight of the UHMWPE or to affect yield of the UHMWPE, or a combination thereof. The method may include altering a flow rate of the AFA co-catalyst provided to the reactor or a flow rate of the catalyst provided to the reactor, or both, to adjust a molar ratio of Al to titanium (Ti) fed to the reactor to give a molecular weight of the UHMWPE or to affect an amount of UHMWPE produced. The method may include discharging a product stream having 1-butene from the separator (e.g., filter) and removing heavy components from the product stream. In certain examples, the heavy components may be removed from the product stream via a thin-film evaporator. The method may include removing ethylene from the product stream in a first distillation column after removing the heavy components from the product stream, wherein the removed ethylene discharges overhead from the first distillation column. The method may include recycling the removed ethylene to the reactor. As indicated, the aforementioned removing of the heavy components may involve processing the product stream in a thin-film evaporator operationally disposed between the separator (e.g., filter) and the first distillation column. The method may include discharging the product stream as a bottoms stream from the first distillation column to a second distillation column, removing second heavy components from the product stream in the second distillation column as a heavy bottoms stream, and discharging 1-butene overhead from the second distillation column as product.

Yet another embodiment is a method for producing 1-butene and UHMWPE, including combining (e.g., reacting) an AFC and a co-catalyst (aluminum alkyl) to give an AFA co-catalyst having the structure:

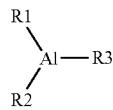

or its dimeric form, wherein Al is aluminum and R1, R2, and R3 are chemical groups. The method includes providing the AFA co-catalyst, a catalyst (titanate compound), and ethylene to a reactor, wherein the catalyst comprises a titanate compound and is provided separate from the AFA co-catalyst. The method includes oligomerizing ethylene in the reactor via the catalyst and the AFA co-catalyst, the oligomerizing including dimerizing ethylene into 1-butene and polymerizing ethylene into UHMWPE. The method includes discharging a product slurry from the reactor, the product slurry including 1-butene and UHMWPE. The method includes removing (e.g., filtering) UHMWPE from the product slurry as coproduct. Removing UHMWPE from the product slurry may give a product stream having 1-butene, and wherein the method further includes processing the product stream to give 1-butene as product. In certain examples, the method may include providing the 1-butene as a comonomer to a polyethylene plant having a polymerization reactor for polymerization of ethylene into polyethylene.

The processing the product stream may include: (1) removing first heavy components from the product stream; (2) removing unreacted ethylene from the product stream in a first distillation column, wherein the unreacted ethylene removed discharges overhead from the first distillation column, and wherein the product stream discharges as a bottoms stream from the first distillation column to a second distillation column; and (3) removing second heavy components from the product stream in the second distillation column as a heavy bottoms stream and discharging 1-butene overhead from the second distillation column as product. The removing of the first heavy components may include removing the first heavy components from the product stream in a thin-film evaporator operationally disposed upstream of the first distillation column.

The method may include adjusting a molar ratio of the AFA co-catalyst to catalyst titanium (Ti) fed to the reactor to affect a property or amount of the UHMWPE. The method may include adjusting a molar ratio of AFC to Ti to affect a property or amount of the UHMWPE, wherein the molar ratio is based on molar rate of AFC combined with the co-catalyst and on molar rate of Ti in the catalyst fed to the reactor. In implementations, the molecular weight of the UHMWPE varies inversely with the molar ratio. The method may include adjusting a feed molar ratio of Ti to aluminum (Al) to the reactor to affect a property or amount of the UHMWPE. The adjusting of this feed molar ratio may involve adjusting a flow rate of the AFA co-catalyst provided to the reactor or adjusting a flow rate of the catalyst provided to the reactor, or both. The adjusting of this feed molar ratio may involve adjusting a ratio of the AFA co-catalyst to the catalyst provided to the reactor. The adjusting this feed molar ratio may involve adjusting a ratio of the AFC to the co-catalyst in the combining of the AFC with the co-catalyst to give the AFA co-catalyst.

Yet another embodiment is a system for producing 1-butene and UHMWPE. The system includes a reactor to oligomerize ethylene in presence of a catalyst (a titanate compound) and an AFA co-catalyst to 1-butene and UHMWPE. The reactor may be a vessel that operates as a bubble-point reactor. The AFA co-catalyst has the structure:

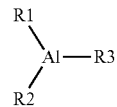

or its dimeric form, wherein Al is aluminum, and wherein R1, R2, and R3 are chemical groups. The system may include a pump to provide the AFA co-catalyst to the reactor and to adjust an amount of the AFA co-catalyst provided to the reactor to alter a property of the UHMWPE. The system may include a control valve to modulate an amount of the AFA co-catalyst provided to the reactor to affect a property or amount of the UHMWPE. A recycle conduit may divert a portion of the effluent discharged from the reactor through a heat exchanger (e.g., a shell-and-tube heat exchanger) back to the reactor for temperature control of the reactor. The system includes a separator (e.g., filter, centrifuge, etc.) to receive effluent from the reactor and remove UHMWPE from the effluent as a coproduct and discharge a product stream having 1-butene. A separation system (having a distillation column) may be included that processes the product stream to discharge 1-butene as product. In implementations with the aforementioned separator as a filter for removing the UHMWPE, the filter may be a disc filter, a mesh filter, or a plate filter.

A number of implementations have been described. Nevertheless, it will be understood that various modifications may be made without departing from the spirit and scope of the disclosure.

What is claimed is:

1. A method for producing 1-butene and ultra-high-molecular-weight polyethylene (UHMWPE) via an antifouling agent (AFA) system, comprising:
feeding a catalyst, an AFA co-catalyst, and ethylene to a reactor, wherein the catalyst comprises a titanate compound, and wherein the AFA co-catalyst comprises the structure:

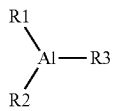

or its dimeric form, wherein Al is aluminum, and wherein R1, R2, and R3 are chemical groups;
dimerizing ethylene into 1-butene in the reactor;
polymerizing ethylene into polyethylene comprising UHMWPE in the reactor;
discharging an effluent from the reactor, the effluent comprising 1-butene and UHMWPE; and
removing UHMWPE from the effluent as coproduct UHMWPE.

2. The method of claim 1, comprising adjusting a molar ratio of the AFA co-catalyst to titanium (Ti) fed to the reactor to affect molecular weight of the polyethylene to give the UHMWPE, wherein the molecular weight of the polyethylene varies inversely with the molar ratio of the AFA co-catalyst to Ti.

3. The method of claim 1, wherein removing comprises filtering UHMWPE from the effluent as coproduct UHMWPE.

4. The method of claim 1, comprising treating the coproduct UHMWPE with acid to remove metal residues comprising aluminum and titanium from the coproduct UHMWPE.

5. The method of claim 1, comprising pelletizing the coproduct UHMWPE.

6. The method of claim 1, comprising combining an antifouling compound (AFC) and a co-catalyst to give the AFA co-catalyst, wherein the co-catalyst comprises an aluminum alkyl, and wherein feeding the catalyst comprises feeding the catalyst to the reactor separate from the AFA co-catalyst.

7. The method of claim 6, comprising adjusting a ratio of a molar rate of the AFC combined with the co-catalyst to a molar rate of Ti in the catalyst fed to the reactor to affect molecular weight of the UHMWPE, wherein the molecular weight of the UHMWPE varies inversely with the ratio.

8. The method of claim 6, wherein the AFC comprises at least one of a phosphonium, a sulfonate, or a sulfonium.

9. The method of claim 6, wherein the AFC comprises a tetraalkyl phosphonium halide, a phosphonium malonate, a trihexyltetradecylphosphonium halide, a tetrabutylphosphonium halide, a tetrabutylphosphonium tetrahaloborate, a tetrabutylphosphonium hexahalophosphate, sodium dodecylbenzenesulfonate, sodium dioctylsulfosuccinate, tetrabutylphosphonium methanesulfonate, tetrabutylphosphonium p-toluenesulfonate, hexadecyltrimethylammonium p-toluenesulfonate, 3-(dimethyl(octadecyl)ammonio)propane-1-sulfonate, 3,3'-(1,4-didodecylpiperazine-1,4-diium-1,4-diyl)bis(propane-1-sulfonate), or 3-(4-(tert-butyl)pyridinio)-1-propanesulfonate, or combinations thereof.

10. The method of claim 6, comprising adjusting a feed molar ratio of Ti to aluminum (Al) to the reactor to affect molecular weight of the polyethylene to give the UHMWPE or to affect an amount of UHMWPE produced, or a combination thereof.

11. The method of claim 1, wherein at least one of R1, R2, or R3 are an antifouling group comprising the structure —O((CH2)nO)mR4, wherein:
n is an integer in a range of 1 to 20;
m is an integer in a range of 1 to 100;
R4 is a hydrocarbyl group, wherein the chemical groups R1, R2, or R3 that are not an antifouling group, if any, are a hydrocarbyl group.

12. A method of producing 1-butene and ultra-high-molecular-weight polyethylene (UHMWPE) utilizing an antifouling agent (AFA) system, comprising:
reacting an antifouling compound (AFC) with a co-catalyst comprising aluminum alkyl to give an AFA co-catalyst;
providing the AFA co-catalyst, a catalyst, and ethylene to a reactor, wherein the catalyst comprises a titanate compound and is provided separate from the AFA co-catalyst;
oligomerizing ethylene in the reactor via the catalyst and the AFA co-catalyst, the oligomerizing comprising dimerizing ethylene into 1-butene and polymerizing ethylene into UHMWPE;
discharging a product slurry from the reactor to a separator, the product slurry comprising 1-butene and UHMWPE; and
removing UHMWPE from the product slurry via the separator as a coproduct.

13. The method of claim 12, wherein the AFC comprises at least one of a phosphonium, a sulfonate, or a sulfonium.

14. The method of claim 12, wherein the AFA co-catalyst comprises the structure:

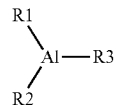

or its dimeric form, wherein Al is aluminum and R1, R2, and R3 are chemical groups.

15. The method of claim 14, wherein at least one of the chemical groups R1, R2, or R3 are an antifouling group comprising at least one of a phosphonium moiety, a sulfonate moiety, or a sulfonium moiety, and wherein the chemical groups R1, R2, or R3 that are not an antifouling group, if any, are a hydrocarbyl group.

16. The method of claim 12, comprising altering a flow rate of the AFA co-catalyst provided to the reactor or a flow rate of the catalyst provided to the reactor, or both, to adjust a molar ratio of the AFA co-catalyst to titanium (Ti) fed to the reactor to affect a molecular weight of the UHMWPE or to affect yield of the UHMWPE, or a combination thereof.

17. The method of claim 12, comprising altering a flow rate of the AFA co-catalyst provided to the reactor or a flow rate of the catalyst provided to the reactor, or both, to adjust a molar ratio of Al to titanium (Ti) fed to the reactor to give a molecular weight of the UHMWPE or to affect an amount of UHMWPE produced.

18. The method of claim 12, comprising:
discharging a product stream comprising 1-butene from the separator, wherein the separator comprises a filter; and
removing heavy components from the product stream.

19. The method of claim 18, wherein removing the heavy components comprises removing the heavy components from the product stream in a thin-film evaporator.

20. The method of claim 18, comprising removing ethylene from the product stream in a first distillation column after removing the heavy components from the product stream, wherein removed ethylene is discharged overhead from the first distillation column.

21. The method of claim 20, comprising recycling the removed ethylene to the reactor.

22. The method of claim 20, wherein removing the heavy components comprises processing the product stream in a thin-film evaporator operationally disposed between the filter and the first distillation column.

23. The method of claim 20, comprising:
discharging the product stream as a bottoms stream from the first distillation column to a second distillation column; and
removing second heavy components from the product stream in the second distillation column as a heavy bottoms stream; and
discharging 1-butene overhead from the second distillation column as product.

24. A method for producing 1-butene and ultra-high-molecular-weight polyethylene (UHMWPE), comprising:
combining an antifouling compound (AFC) and a co-catalyst comprising aluminum alkyl to give an antifouling agent (AFA) co-catalyst, wherein the AFA co-catalyst comprises the structure:

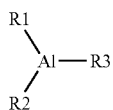

or its dimeric form, wherein Al is aluminum and R1, R2, and R3 are chemical groups;
providing the AFA co-catalyst, a catalyst, and ethylene to a reactor, wherein the catalyst comprises a titanate compound and is provided separate from the AFA co-catalyst;
oligomerizing ethylene in the reactor via the catalyst and the AFA co-catalyst, the oligomerizing comprising dimerizing ethylene into 1-butene and polymerizing ethylene into UHMWPE;
discharging a product slurry from the reactor, the product slurry comprising 1-butene and UHMWPE; and
removing UHMWPE from the product slurry as coproduct.

25. The method of claim 24, wherein combining the AFC with the co-catalyst comprises reacting the AFC with the co-catalyst, and wherein removing UHMWPE comprises filtering the UHMWPE from the product slurry.

26. The method of claim 24, wherein removing UHMWPE from the product slurry gives a product stream comprising 1-butene, and wherein the method further comprises processing the product stream to give 1-butene as product.

27. The method of claim 26, comprising further providing the 1-butene as a comonomer to a polyethylene plant comprising a polymerization reactor for polymerization of ethylene into polyethylene.

28. The method of claim 26, wherein processing the product stream comprises:
removing first heavy components from the product stream;
removing unreacted ethylene from the product stream in a first distillation column, wherein the unreacted ethylene removed is discharged overhead from the first distillation column, and wherein the product stream is discharged as a bottoms stream from the first distillation column to a second distillation column; and
removing second heavy components from the product stream in the second distillation column as a heavy bottoms stream and discharging 1-butene overhead from the second distillation column as product.

29. The method of claim 28, wherein removing the first heavy components comprises removing the first heavy components from the product stream in a thin-film evaporator operationally disposed upstream of the first distillation column.

30. The method of claim 24, wherein at least one of the chemical groups R1, R2, or R3 are an antifouling group comprising the structure —O((CH2)nO)mR4, where:
n is an integer in a range of 1 to 20;
m is an integer in a range of 1 to 100;
R4 is a hydrocarbyl group, wherein the chemical groups R1, R2, or R3 that are not an antifouling group, if any, are a hydrocarbyl group.

31. The method of claim 24, comprising adjusting a feed molar ratio of titanium (Ti) to aluminum (Al) to the reactor to affect a property or amount of the UHMWPE.

32. The method of claim 31, wherein adjusting the feed molar ratio comprises adjusting a flow rate of the AFA co-catalyst provided to the reactor or adjusting a flow rate of the catalyst provided to the reactor, or both.

33. The method of claim 31, wherein adjusting the feed molar ratio comprises adjusting a ratio of the AFA co-catalyst to the catalyst provided to the reactor.

34. The method of claim 31, wherein adjusting the feed molar ratio comprises adjusting a ratio of the AFC to the co-catalyst in the combining of the AFC with the co-catalyst to give the AFA co-catalyst.

35. The method of claim 24, comprising adjusting a molar ratio of the AFA co-catalyst to Ti fed to the reactor to affect a property or amount of the UHMWPE.

36. The method of claim 24, comprising adjusting a molar ratio of AFC to Ti to affect a property or amount of the UHMWPE, wherein the molar ratio is based on molar rate of the AFC combined with the co-catalyst and on molar rate of Ti in the catalyst fed to the reactor.

37. The method of claim 36, wherein molecular weight of the UHMWPE varies inversely with the molar ratio.

38. A system for producing 1-butene and ultra-high-molecular-weight polyethylene (UHMWPE), comprising:
a reactor to oligomerize ethylene in presence of a catalyst and an antifouling agent (AFA) co-catalyst to 1-butene and UHMWPE, wherein the catalyst comprises a titanate compound, and wherein the AFA co-catalyst comprises the structure:

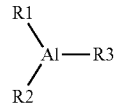

or its dimeric form, wherein Al is aluminum, and wherein R1, R2, and R3 are chemical groups;

a separator comprising a filter to receive an effluent from the reactor and remove UHMWPE from the effluent as a coproduct and to discharge a product stream comprising 1-butene; and a catalyst removal section downstream of the separator.

39. The system of claim 38, wherein the reactor comprises a vessel to operate as a bubble-point reactor.

40. The system of claim 39, wherein the filter comprises a disc filter, a mesh filter, or a plate filter.

41. The system of claim 38, comprising a separation system to process the product stream to discharge 1-butene as product, wherein the separation system comprises a distillation column.

42. The system of claim 38, comprising a recycle conduit to divert a portion of the effluent through a heat exchanger back to the reactor for temperature control of the reactor.

43. The system of claim 42, wherein the heat exchanger comprises a shell-and-tube heat exchanger.

44. The system of claim 38, comprising a pump to provide the AFA co-catalyst to the reactor and to adjust an amount of the AFA co-catalyst provided to the reactor to alter a property of the UHMWPE.

45. The system of claim 38, comprising a control valve to modulate an amount of the AFA co-catalyst provided to the reactor to affect a property or amount of the UHMWPE.

\* \* \* \* \*